US008993511B2

(12) United States Patent
Yamashita et al.

(10) Patent No.: US 8,993,511 B2
(45) Date of Patent: Mar. 31, 2015

(54) β-ARRESTIN EFFECTORS AND COMPOSITIONS AND METHODS OF USE THEREOF

(71) Applicant: Trevena, Inc., King of Prussia, PA (US)

(72) Inventors: Dennis Yamashita, Cambridge, MA (US); Xiao-Tao Chen, Furlong, PA (US)

(73) Assignee: Trevena, Inc., King of Prussia, PA (US)

( * ) Notice: Subject to any disclaimer, the term of this patent is extended or adjusted under 35 U.S.C. 154(b) by 0 days.

(21) Appl. No.: 14/449,647

(22) Filed: Aug. 1, 2014

(65) Prior Publication Data

US 2014/0336123 A1    Nov. 13, 2014

Related U.S. Application Data

(60) Continuation of application No. 13/926,766, filed on Jun. 25, 2013, now Pat. No. 8,796,204, which is a division of application No. 12/647,810, filed on Dec. 28, 2009, now Pat. No. 8,486,885.

(60) Provisional application No. 61/141,126, filed on Dec. 29, 2008.

(51) Int. Cl.
*A61K 38/00* (2006.01)
*A61P 13/12* (2006.01)
*A61P 9/00* (2006.01)
*C07K 7/06* (2006.01)
*A61K 38/08* (2006.01)
*C07K 7/14* (2006.01)

(52) U.S. Cl.
CPC . *C07K 7/06* (2013.01); *A61K 38/08* (2013.01); *C07K 7/14* (2013.01)
USPC .......................... 514/1.1; 514/15.4; 514/16.4

(58) Field of Classification Search
None
See application file for complete search history.

(56) References Cited

U.S. PATENT DOCUMENTS

| | | | |
|---|---|---|---|
| 3,932,624 | A | 1/1976 | Fulton |
| 4,115,538 | A | 9/1978 | Satoh et al. |
| 4,547,489 | A | 10/1985 | Goldstein et al. |
| 5,112,807 | A | 5/1992 | Hamano et al. |
| 5,182,264 | A | 1/1993 | Watkins |
| 5,436,128 | A | 7/1995 | Harpold et al. |
| 5,629,292 | A | 5/1997 | Rodgers et al. |
| 5,958,884 | A | 9/1999 | Kifor et al. |
| 2003/0017970 | A1 | 1/2003 | Rodgers et al. |
| 2004/0214836 | A1 | 10/2004 | Cheresh et al. |
| 2005/0202029 | A1 | 9/2005 | Zabel et al. |
| 2007/0286863 | A1 | 12/2007 | Sinal et al. |
| 2009/0280113 | A1 | 11/2009 | Graham et al. |
| 2010/0092974 | A1 | 4/2010 | Zabel et al. |
| 2010/0150990 | A1 | 6/2010 | Greaves et al. |
| 2010/0184701 | A1 | 7/2010 | Yamashita et al. |

FOREIGN PATENT DOCUMENTS

| | | |
|---|---|---|
| EP | 0498361 | 8/1992 |
| WO | 9003181 | 4/1990 |
| WO | 9203145 | 3/1992 |
| WO | 9213564 | 8/1992 |
| WO | 9614858 | 5/1996 |
| WO | 9963930 | 12/1999 |
| WO | 2008018792 | 2/2008 |
| WO | 2010077339 | 7/2010 |
| WO | 2011035332 | 3/2011 |

OTHER PUBLICATIONS

Parlee et al., "Serum chemerin levels vary with time of day and are modified by obesity and tumor necrosis factor-{alpha}," Endocrinology (2010) 151 (6):2590-2602.
Meder et al., "Characterization of human circulating TIG2 as a ligand for the orphan receptor ChemR23," FEBS Letters (2003) 555(3):495-499.
Gantz et al., "Molecular cloning of a novel receptio (CMKLR1) with homology to the chemotactic factor receptors," Cytogenet Cell Genet (1996) 74 (4):286-290.
Patel et al., "Beta-Arrestin-Mediated Signaling in the Heart", NIH Public Access, Author Manuscript, Circ J., (2008) 72 (11): 1725-1729.
Violin, J. et al., "Beta-arrestin-biased ligands at seven-transmembrane receptors." Trends Pharmacal Sci., 2007, 28 (8):416-422.
Kenakin, T., "Functional selectivity and biased receptor signaling", J Pharmacal Exp Ther., 2011, 336(2):296-302.
Dell'Italia, L., "Translational success stories: angiotensin receptor 1 antagonists in heart failure", Circ Res., 2011, 109 (4):437-452.
DeWire, S. et al., "Biased ligands for better cardiovascular drugs: dissecting G-protein-coupled receptor pharmacology", Circ Res., 2011, 109(2):205-216.
Rajagopal, S. et al., "Quantifying Ligand Bias at Seven-Transmembrane Receptors. Molecular Pharmacology", 2011, 80(3):367-377.
Notice of Allowance and Fee(s) Due for U.S. Appl. No. 13/755,637, Sep. 30, 2014.
Information Disclosure Statement Communication dated Oct. 13, 2014.
Information Disclosure Statement Communication from Applicants dated Mar. 3, 2014.
Non-Final Office Action dated Dec. 2, 2013 received in co-pending U.S. Appl. No. 13/925,170.
Non-Final Office Action dated Oct. 15, 2013 received in related U.S. Appl. No. 13/755,637.
Samanen et al. "Potent angiotensin II antagonists with non-beta-branched amino acids in position 5", J. Medicinal Chemistry, 1989, 32, 466-4 72.

(Continued)

*Primary Examiner* — Marcela M Cordero Garcia
*Assistant Examiner* — Sergio Coffa
(74) *Attorney, Agent, or Firm* — Pepper Hamilton LLP

(57) ABSTRACT

This application describes a family of compounds acting as β-arrestin effectors. Such compounds may provide significant therapeutic benefit in the treatment of chronic and acute cardiovascular diseases.

25 Claims, No Drawings

(56) References Cited

OTHER PUBLICATIONS

Samanen et al. "An investigation of angiotensin II agonist and antagonist analogs with 5,5-dimethylthiazolidine-4-carboxylic acid and other constrained amino acids", J. Medicinal Chemistry, 1991, 34, 3036-3043.

Aumelas, A. et al., "Studies on Angiotens in II and Analogs: Impact of Substitution in Position 8 on Conformation and Activity", Proc. Natl. Acad. Sci., 1985, 82:1881-1885.

Schoelkens, B.A. et al., "1,8 Disubstituted analogues of [Ile<5>] and [Val<5>] angiotensin II: difference in potency and specificity of angiotensin II antagonistic activity", Hoppe-Seyler's Zeitschrift Fur Physiologische Chemie, 357:825-838, 1976.

Violin et al, Selectively engaging b-arrestins at the angiotensin II type 1 receptor reduces blood pressure and increases cardiac performance, The Journal of Pharmacology and Experimental Therapeutics, vol. 335 No. 3 pp. 572-579, 2012.

Samanen J et al, Effects of d-amino acid substitution on antagonist activities of angiotensin II analogues, Journal of Medicinal Chemistry, 1998 31:510-516.

Ackerman et al., "Ion channels—basic science and clinical disease," New Eng l J Med (1997) 336(22): 1575-1595.

Barak et al., "Internal trafficking and surface mobility of a functionally intact beta2-adrenergic receptor-green fluorescent protein conjugate," Mol Pharmacal (1997) 51 (2):177-184.

Berridge et al., "Inositol trisphosphate, a novel second messenger in cellular signal transduction," Nature (1984) 312 (5992):315-321.

Bohn et al., "Mu-opioid receptor desensitization by beta-arrestin-2 determines morphine tolerance but not dependence," Nature (2000) 408(6813):720-723.

Bourne et al., "The GTPase superfamily: conserved structure and molecular mechanism," Nature (1991) 349 (6305):117-127.

Bourne et al., "The GTPase superfamily: a conserved switch for diverse cell functions," Nature (1990) 348 (6297): 125-132.

Conway et al, "Quantitative analysis of agonist-dependent parathyroid hormone receptor trafficking in whole cells using a functional green fluorescent protein conjugate," J Cell Physiol (2001) 189(3):341-355.

Daniel et al., "Screening for potassium channel modulators by a high through-put 86-rubidium efflux assay in a 96-well microtiter plate," J Pharmacal Meth (1991) 25(3): 185-193.

Felley-Bosco et al., "Constitutive expression of inducible nitric oxide synthase in human bronchial epithelial cells induces c-fos and stimulates the cGMP pathway," Am J Resp Cell and Mol Biol (1994) 11 (2):159-164.

Gonzales et al., "Improved indicators of cell membrane potential that use fluorescence resonance energy transfer," Chern Biol (1997) 4(4):269-277.

Groarke et al., "Visualization of agonist-induced association and trafficking of green fluorescent protein-tagged forms o both beta-arrestin-1 and the thyrotropin-releasing hormone receptor-1 ," J Biol Chern (1999) 274(33):23263-23269.

Hamill et al., "Improved patch-clamp techniques for high-resolution current recording from cells and cell-free membrane patches," PFlugers Archiv (1981) 391(2):85-100.

Holevinsky et al., "ATP-sensitive K+ channel opener acts as a potent Cl– channel inhibitor in vascular smooth muscle cells," J Membrane Biology (1994) 137(1):57-70.

Kroeger et al., "Constitutive and agonist-dependent homo-oligomerization of the thyrotropin-releasing hormone receptor. Detection in living cells using bioluminescence resonance energy transfer," J Biol Chern (2001) 276 (16): 12736-12743.

Merrifield et al., "Solid Phase Peptide Synthesis. I. The Synthesis of a Tetrapeptide," J Am Chern Soc. (1963) 85 (14):2149.

Mistili et al., "Applications of the green fluorescent protein in cell biology and biotechnology", Nature Biotechnology (1997) 15(10):961-964.

Offermans et al., "G alpha 15 and G alpha 16 couple a wide variety of receptors to phospholipase C.," J Biol Chern (1995) 270(25): 15175-15180.

Pitcher et al., "G protein-coupled receptor kinases," Annu Rev Biochem (1998) 67:653-692.

Rattan et al., "Protein synthesis, posttranslational modifications, and aging," Ann NY Acad Sci (1992) 663:48-62.

Seifter et al., "Analysis for protein modifications and nonprotein cofactors.," Meth Enzymol ( 1990) 182:626-646.

Smith et al., Tritiated D-ala1-peptide T binding: A pharmacologic basis for the design of drugs which inhibit HIV receptor binding, Drug Development Res (1988) 15:371-379.

Traynor et al., "Modulation by mu-opioid agonists of guanosine-5'-0-(3-[35S]thio)triphosphate binding to membranes from human neuroblastoma SH-SY5Y cells," Mol Pharmacal (1995) 47(4):848-854.

Vestergarrd-Bogind et al., "Single-file diffusion through the Ca2+-activated K+ channel of human red cells" J Membrane Biol (1985) 88(1):67-75.

Vrecl et al., "Agonist-induced endocytosis and recycling of the gonadotropin-releasing hormone receptor: effect of beta-arrestin on internalization kinetics," Mol Endocrinol (1996) 12:1818-1829.

Wilkie et al., "Characterization of G-protein alpha subunits in the Gq class: expression in murine tissues and in stromal and hematopoietic cell lines," Proc Nat'l Acad Sci USA (1991) 88(22):1 0049-10053.

Sasaki et al., "Solid phase synthesis of peptides containing the CH2NH peptide bond isostere," Peptides (1987) 8 (1):119-121.

Fehrentz et al., "An efficient synthesis of optically active alpha-(t-Butoxycarbonylamino)-aldehydes from alpha-amino acids," Synthesis (1983) pp. 676-678.

Wittamer et al., "The C-terminal nonapeptide of mature chemerin activates the chemerin receptor with low nanomolar potency," Journal of Biological Chemistry (2004) 279(11 ):9956-9962.

Shimamura et al., "Identification of a stable chemerin analog with potent activity toward ChemR23," Peptides (2009) 30:1529-1538.

Cash et al., "Synthetic chemerin-derived peptides suppress inflammation through ChemR23," Journal of Experimental Medicine (2008) 2005(4):767-775.

Barnea et al., "The genetic design of signaling cascades to record receptor activation," PNAS (2008) 105(1):64-69.

Ernst et al., "Chemerin: at the crossroads of inflammation and obesity," Cell (2010) pp. 1-8.

Luangsay et al., "Mouse ChemR23 is expressed in dendritic cell subsets and macrophages, and mediates an anti-inflammatory activity of chemerin in a lung disease model," Journal of Immunology (2009) 183:6489-6499.

Sell et al., "Chemerin is a novel adipocyte-derived factor inducing insulin resistance in primary human skeletal muscle cells," Diabetes (2009) 58(12):2731-2740.

Wollenberg et al., "Plasmacytoid dendritic cells: a new cutaneous dendritic cell subset with distinct role in inflammatory skin diseases," Journal of Investigative Dermatology (2002) 119(5): 1096-1102.

Zabel et al., "Chemokine-like receptor 1 expression and chemerin-directed chemotaxis distinguish plasmacytoid from myeloid dendritic cells in human blood," Journal of Immunology (2010) 174:244-251.

Zabel et al., "Chemokine-like receptor 1 expression by macrophages in vivo: regulation by TGF-beta and TLR ligands," Experimental Hematology (2006) 34(8): 1106-1114.

Wittamer et al., "Specific recruitment of antigen-presenting cells by chemerin, a novel processed ligand from human inflammatory fluids," Journal of Experimental Medicine (2003) 198(7):977-985.

Sozzani et al., "Trafficking properties of plasmacytoid dendritic cells in health and disease," Trends in Immunology (2010) 31:270-277.

Siegal et al., "The nature of the principal type 1 interferon-producing cells in human blood," Science (1999) 284 (5421):1835-1837.

Parolini et al., "The role of chemerin in the colocalization of NK and dendritic cell subsets into inflames tissues," Blood (2007) 555(3):495-499.

SEQUENCE LISTING

```
<160> NUMBER OF SEQ ID NOS: 89

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Arg Val Tyr Ile His Pro Phe
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Sarcosine
<220> FEATURE:
<223> OTHER INFORMATION: C-term amidated

<400> SEQUENCE: 2

Xaa Arg Val Ile Ile His Pro Ile
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine

<400> SEQUENCE: 3

Xaa Arg Val Ile Val His Pro Ile
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine, N-methyl-L-Ala, N-methyl-D-Ala,
      N,N-dimethyl-Gly, L-Asp, D-Asp, L-Glu, D-Glu, N-methyl-L-Asp,
      N-methyl-L-Glu, pyrrolid-1-ylacetic acid or morpholin-4-
      ylaceticacid
<220> FEATURE:
<221> NAME/KEY: MOD_RES
<222> LOCATION: (4)..(4)
<223> OTHER INFORMATION: L-Ile, Gly, L-Tyr, O-methyl-L-Tyr, L-Val,L-Phe,
      3-hydroxy-L-Tyr, 2,6-dimethyl-L-Tyr, 3-fluoro-L-Tyr,
      4-fluorophenyl-L-analine, 2,6-difluoro-L-Tyr, 3-nitro-L-Tyr,
      3,5-dinitro-L-Tyr, 3,5-dibromo-L-Tyr, 3-chloro-L-Tyr,
      O-allyl-L-Tyr or 3,5-diiodo-L-Tyr
<220> FEATURE:
<221> NAME/KEY: MOD_RES
<222> LOCATION: (5)..(5)
<223> OTHER INFORMATION: L-Ile, L-Val, L-Tyr, L-Glu, L-Phe, L-His,
      L-Lys, L-Arg, O-methyl-L-Thr, D-Ala or L-norvaline
<220> FEATURE:
<221> NAME/KEY: MOD_RES
<222> LOCATION: (8)..(8)
<223> OTHER INFORMATION: L-Ile, L-Ile-amide, Gly, Gly-amide,
      L-Ala, L-Ala-amide, D-Ala, D-Phe or L-Norvaline
<220> FEATURE:
<223> OTHER INFORMATION: See specification as filed for detailed
      description of substitutions and preferred embodiments

<400> SEQUENCE: 4

Xaa Arg Val Xaa Xaa His Pro Xaa
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Sarcosine

<400> SEQUENCE: 5

Xaa Arg Val Gly Val His Pro Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<223> OTHER INFORMATION: C-term amidated

<400> SEQUENCE: 6

Xaa Arg Val Gly Val His Pro Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine

<400> SEQUENCE: 7

Xaa Arg Val Tyr Val His Pro Ala
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<223> OTHER INFORMATION: C-term amidated

<400> SEQUENCE: 8

Xaa Arg Val Tyr Val His Pro Ala
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
```

<400> SEQUENCE: 9

Xaa Arg Val Tyr Ile His Pro Ala
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<223> OTHER INFORMATION: C-term amidated

<400> SEQUENCE: 10

Xaa Arg Val Tyr Ile His Pro Ala
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine

<400> SEQUENCE: 11

Xaa Arg Val Tyr Val His Pro Ile
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<223> OTHER INFORMATION: C-term amidated

<400> SEQUENCE: 12

Xaa Arg Val Tyr Val His Pro Ile
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 13

Arg Val Tyr Ile His Pro
1               5

```
<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine

<400> SEQUENCE: 14

Xaa Arg Val Tyr Tyr His Pro Ile
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<223> OTHER INFORMATION: C-term amidated

<400> SEQUENCE: 15

Xaa Arg Val Tyr Tyr His Pro Ile
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine

<400> SEQUENCE: 16

Xaa Arg Val Tyr Glu His Pro Ile
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: L-Tyr, 3-hydroxy-L-Tyr, 3-fluoro-L-Tyr,
      2,6-difluoro-L-Tyr, 3-nitro-L-Tyr, 3,5-dinitro-L-Tyr or
      3-chloro-L-Tyr
<220> FEATURE:
<221> NAME/KEY: MOD_RES
<222> LOCATION: (5)..(5)
<223> OTHER INFORMATION: L-Ile, L-Lys or O-Methyl-L-Thr
```

```
<220> FEATURE:
<221> NAME/KEY: MOD_RES
<222> LOCATION: (8)..(8)
<223> OTHER INFORMATION: D-Ala or L-Ala
<220> FEATURE:
<223> OTHER INFORMATION: See specification as filed for detailed
      description of substitutions and preferred embodiments

<400> SEQUENCE: 17

Xaa Arg Val Xaa Xaa His Pro Xaa
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: L-Tyr, 3-hydroxy-L-Tyr, 3-fluoro-L-Tyr or
      3-chloro-L-Tyr
<220> FEATURE:
<221> NAME/KEY: MOD_RES
<222> LOCATION: (5)..(5)
<223> OTHER INFORMATION: O-Methyl-L-Thr
<220> FEATURE:
<221> NAME/KEY: MOD_RES
<222> LOCATION: (8)..(8)
<223> OTHER INFORMATION: D-Ala or L-Ala

<400> SEQUENCE: 18

Xaa Arg Val Xaa Xaa His Pro Xaa
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine

<400> SEQUENCE: 19

Xaa Arg Val Tyr Tyr His Pro Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine

<400> SEQUENCE: 20

Xaa Arg Val Tyr Glu His Pro Ala
1               5
```

```
<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine

<400> SEQUENCE: 21

Xaa Arg Val Tyr Phe His Pro Ala
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine

<400> SEQUENCE: 22

Xaa Arg Val Tyr His His Pro Ala
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine

<400> SEQUENCE: 23

Xaa Arg Val Tyr Lys His Pro Ala
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine

<400> SEQUENCE: 24

Xaa Arg Val Tyr Arg His Pro Ala
1               5

<210> SEQ ID NO 25
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 25

Asp Arg Val Tyr Ile His Pro Ala
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<223> OTHER INFORMATION: C-term amidated

<400> SEQUENCE: 26

Xaa Arg Val Tyr Tyr His Pro
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (8)..(8)
<223> OTHER INFORMATION: D-Ala

<400> SEQUENCE: 27

Xaa Arg Val Tyr Ile His Pro Ala
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (8)..(8)
<223> OTHER INFORMATION: D-Phe

<400> SEQUENCE: 28

Xaa Arg Val Tyr Tyr His Pro Phe
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                                 peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: O-methyl-Tyr

<400> SEQUENCE: 29

Xaa Arg Val Tyr Ile His Pro Ala
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (5)..(5)
<223> OTHER INFORMATION: O-methyl-Thr

<400> SEQUENCE: 30

Xaa Arg Val Tyr Thr His Pro Ala
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N,N-dimethyl-Gly

<400> SEQUENCE: 31

Gly Arg Val Tyr Val His Pro Ala
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N,N-dimethyl-Gly

<400> SEQUENCE: 32

Gly Arg Val Tyr Ile His Pro Ala
1               5

<210> SEQ ID NO 33
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl-L-Ala

<400> SEQUENCE: 33

Ala Arg Val Tyr Val His Pro Ala
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl-L-Ala

<400> SEQUENCE: 34

Ala Arg Val Tyr Ile His Pro Ala
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (8)..(8)
<223> OTHER INFORMATION: Norvaline

<400> SEQUENCE: 35

Xaa Arg Val Tyr Ile His Pro Xaa
1               5

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(18)
<223> OTHER INFORMATION: cyclic

<400> SEQUENCE: 36

Arg Val Tyr Ile His Pro Arg Val Tyr Ile His Pro Arg Val Tyr Ile
1               5                   10                  15

His Pro

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: misc_feature
<222> LOCATION: (1)..(18)
<223> OTHER INFORMATION: cyclic

<400> SEQUENCE: 37

Phe Val Tyr Ile His Pro Phe Val Tyr Ile His Pro Phe Val Tyr Ile
1               5                   10                  15

His Pro

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: cyclic

<400> SEQUENCE: 38

Val Tyr Ile His Pro Phe
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: L-Tyr, 3-hydroxy-L-Tyr, 3-fluoro-L-Tyr,
      2,6-difluoro-L-Tyr, 3-nitro-L-Tyr, 3,5-dinitro-L-Tyr or
      3-chloro-L-Tyr
<220> FEATURE:
<223> OTHER INFORMATION: C-term amidated

<400> SEQUENCE: 39

Xaa Arg Val Xaa Tyr His Pro
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<223> OTHER INFORMATION: C-term amidated

<400> SEQUENCE: 40

Xaa Arg Val Tyr Glu His Pro
1               5

<210> SEQ ID NO 41
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<223> OTHER INFORMATION: C-term amidated

<400> SEQUENCE: 41

Xaa Arg Val Tyr Phe His Pro
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<223> OTHER INFORMATION: C-term amidated

<400> SEQUENCE: 42

Xaa Arg Val Tyr His His Pro
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<223> OTHER INFORMATION: C-term amidated

<400> SEQUENCE: 43

Xaa Arg Val Tyr Lys His Pro
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl-L-Ala
<220> FEATURE:
<221> NAME/KEY: MOD_RES
<222> LOCATION: (8)..(8)
<223> OTHER INFORMATION: D-Ala

<400> SEQUENCE: 44

Ala Arg Val Tyr Ile His Pro Ala
1               5
```

```
<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<223> OTHER INFORMATION: C-term amidated

<400> SEQUENCE: 45

Xaa Arg Val Tyr Arg His Pro
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl-L-Ala
<220> FEATURE:
<221> NAME/KEY: MOD_RES
<222> LOCATION: (8)..(8)
<223> OTHER INFORMATION: D-Ala

<400> SEQUENCE: 46

Ala Arg Val Tyr Ile His Pro Ala
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl-D-Ala

<400> SEQUENCE: 47

Ala Arg Val Tyr Ile His Pro Ala
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (8)..(8)
<223> OTHER INFORMATION: D-Ala

<400> SEQUENCE: 48
```

```
Xaa Arg Val Phe Ile His Pro Ala
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (8)..(8)
<223> OTHER INFORMATION: D-Ala

<400> SEQUENCE: 49

Xaa Lys Val Tyr Ile His Pro Ala
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (8)..(8)
<223> OTHER INFORMATION: D-Ala

<400> SEQUENCE: 50

Xaa Arg Val Tyr Ile Lys Pro Ala
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (7)..(7)
<223> OTHER INFORMATION: D-Pro
<220> FEATURE:
<223> OTHER INFORMATION: C-term amidated

<400> SEQUENCE: 51

Xaa Arg Val Tyr Ile His Pro
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (1)..(1)
<223> OTHER INFORMATION: Sarcosine

<400> SEQUENCE: 52

Xaa Arg Val Tyr Tyr His Pro
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (5)..(5)
<223> OTHER INFORMATION: D-Ala
<220> FEATURE:
<223> OTHER INFORMATION: C-term amidated

<400> SEQUENCE: 53

Xaa Arg Val Tyr Ala His Pro
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine

<400> SEQUENCE: 54

Xaa Arg Val Tyr Val His Pro
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<223> OTHER INFORMATION: C-term amidated

<400> SEQUENCE: 55

Xaa Arg Val Tyr Val His
1               5

<210> SEQ ID NO 56
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 56

Asp Arg Val Tyr Ile His Pro Gly
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 57

Asp Arg Val Tyr Tyr His Pro
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Asp
<220> FEATURE:
<223> OTHER INFORMATION: C-term amidated

<400> SEQUENCE: 58

Asp Arg Val Tyr Tyr His Pro
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 59

Glu Arg Val Tyr Tyr His Pro
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Glu
<220> FEATURE:
<223> OTHER INFORMATION: C-term amidated

<400> SEQUENCE: 60

Glu Arg Val Tyr Tyr His Pro
1               5
```

```
<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl-L-Asp
<220> FEATURE:
<223> OTHER INFORMATION: C-term amidated

<400> SEQUENCE: 61

Asp Arg Val Tyr Tyr His Pro
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl-L-Glu
<220> FEATURE:
<223> OTHER INFORMATION: C-term amidated

<400> SEQUENCE: 62

Glu Arg Val Tyr Tyr His Pro
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 63

Asp Arg Val Tyr Phe His Pro
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 64

Glu Arg Val Tyr Phe His Pro
1               5

<210> SEQ ID NO 65
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl-L-Asp
<220> FEATURE:
<223> OTHER INFORMATION: C-term amidated

<400> SEQUENCE: 65

Asp Arg Val Tyr Phe His Pro
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl-L-Glu
<220> FEATURE:
<223> OTHER INFORMATION: C-term amidated

<400> SEQUENCE: 66

Glu Arg Val Tyr Phe His Pro
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: 3-Hydroxy-L-Tyr
<220> FEATURE:
<221> NAME/KEY: MOD_RES
<222> LOCATION: (8)..(8)
<223> OTHER INFORMATION: D-Ala

<400> SEQUENCE: 67

Xaa Arg Val Tyr Ile His Pro Ala
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: 2,6-Dimethyl-L-Tyr
<220> FEATURE:
<221> NAME/KEY: MOD_RES
<222> LOCATION: (8)..(8)
```

```
<223> OTHER INFORMATION: D-Ala

<400> SEQUENCE: 68

Xaa Arg Val Tyr Ile His Pro Ala
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: 3-fluoro-L-Tyr
<220> FEATURE:
<221> NAME/KEY: MOD_RES
<222> LOCATION: (8)..(8)
<223> OTHER INFORMATION: D-Ala

<400> SEQUENCE: 69

Xaa Arg Val Tyr Ile His Pro Ala
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: 4-fluorophenyl-L-Ala
<220> FEATURE:
<221> NAME/KEY: MOD_RES
<222> LOCATION: (8)..(8)
<223> OTHER INFORMATION: D-Ala

<400> SEQUENCE: 70

Xaa Arg Val Ala Ile His Pro Ala
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: 2,6-difluoro-L-Tyr
<220> FEATURE:
<221> NAME/KEY: MOD_RES
<222> LOCATION: (8)..(8)
<223> OTHER INFORMATION: D-Ala
```

```
<400> SEQUENCE: 71

Xaa Arg Val Tyr Ile His Pro Ala
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: 3-Nitro-L-Tyr
<220> FEATURE:
<221> NAME/KEY: MOD_RES
<222> LOCATION: (8)..(8)
<223> OTHER INFORMATION: D-Ala

<400> SEQUENCE: 72

Xaa Arg Val Tyr Ile His Pro Ala
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: 3,5-Dinitro-L-Tyr
<220> FEATURE:
<221> NAME/KEY: MOD_RES
<222> LOCATION: (8)..(8)
<223> OTHER INFORMATION: D-Ala

<400> SEQUENCE: 73

Xaa Arg Val Tyr Ile His Pro Ala
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: 3,5-Dibromo-L-Tyr
<220> FEATURE:
<221> NAME/KEY: MOD_RES
<222> LOCATION: (8)..(8)
<223> OTHER INFORMATION: D-Ala
```

```
<400> SEQUENCE: 74

Xaa Arg Val Tyr Ile His Pro Ala
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: 3-Chloro-L-Tyr
<220> FEATURE:
<221> NAME/KEY: MOD_RES
<222> LOCATION: (8)..(8)
<223> OTHER INFORMATION: D-Ala

<400> SEQUENCE: 75

Xaa Arg Val Tyr Ile His Pro Ala
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: O-allyl-L-Tyr
<220> FEATURE:
<221> NAME/KEY: MOD_RES
<222> LOCATION: (8)..(8)
<223> OTHER INFORMATION: D-Ala

<400> SEQUENCE: 76

Xaa Arg Val Tyr Ile His Pro Ala
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: 3-Hydroxy-L-Tyr
<220> FEATURE:
<221> NAME/KEY: MOD_RES
<222> LOCATION: (5)..(5)
<223> OTHER INFORMATION: O-methyl-Thr

<400> SEQUENCE: 77
```

```
Xaa Arg Val Tyr Thr His Pro Ala
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: 3-fluoro-L-Tyr
<220> FEATURE:
<221> NAME/KEY: MOD_RES
<222> LOCATION: (5)..(5)
<223> OTHER INFORMATION: O-methyl-Thr

<400> SEQUENCE: 78

Xaa Arg Val Tyr Thr His Pro Ala
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: 3-chloro-L-Tyr
<220> FEATURE:
<221> NAME/KEY: MOD_RES
<222> LOCATION: (5)..(5)
<223> OTHER INFORMATION: O-methyl-Thr

<400> SEQUENCE: 79

Xaa Arg Val Tyr Thr His Pro Ala
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyrrolid-1-ylacetic acid
<220> FEATURE:
<221> NAME/KEY: MOD_RES
<222> LOCATION: (8)..(8)
<223> OTHER INFORMATION: D-Ala

<400> SEQUENCE: 80

Xaa Arg Val Tyr Ile His Pro Ala
1               5
```

```
<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Morpholin-4-ylacetic acid
<220> FEATURE:
<221> NAME/KEY: MOD_RES
<222> LOCATION: (8)..(8)
<223> OTHER INFORMATION: D-Ala

<400> SEQUENCE: 81

Xaa Arg Val Tyr Ile His Pro Ala
1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl-D-Ala
<220> FEATURE:
<221> NAME/KEY: MOD_RES
<222> LOCATION: (8)..(8)
<223> OTHER INFORMATION: D-Ala

<400> SEQUENCE: 82

Ala Arg Val Tyr Ile His Pro Ala
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (5)..(5)
<223> OTHER INFORMATION: Norvaline
<220> FEATURE:
<221> NAME/KEY: MOD_RES
<222> LOCATION: (8)..(8)
<223> OTHER INFORMATION: D-Ala

<400> SEQUENCE: 83

Xaa Arg Val Tyr Xaa His Pro Ala
1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Sarcosine
<220> FEATURE:
<221> NAME/KEY: MOD_RES
<222> LOCATION: (5)..(5)
<223> OTHER INFORMATION: O-methyl-Thr
<220> FEATURE:
<221> NAME/KEY: MOD_RES
<222> LOCATION: (8)..(8)
<223> OTHER INFORMATION: D-Ala

<400> SEQUENCE: 84

Xaa Arg Val Tyr Thr His Pro Ala
1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: 3,5-diiodo-L-Tyr
<220> FEATURE:
<221> NAME/KEY: MOD_RES
<222> LOCATION: (8)..(8)
<223> OTHER INFORMATION: D-Ala

<400> SEQUENCE: 85

Xaa Arg Val Tyr Ile His Pro Ala
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl-L-Ala
<220> FEATURE:
<221> NAME/KEY: MOD_RES
<222> LOCATION: (4)..(4)
<223> OTHER INFORMATION: L-Tyr, 3-hydroxy-L-Tyr, 3-fluoro-L-Tyr,
      2,6-difluoro-L-Tyr, 3-nitro-L-Tyr, 3,5-dinitro-L-Tyr or
      3-chloro-L-Tyr
<220> FEATURE:
<221> NAME/KEY: MOD_RES
<222> LOCATION: (5)..(5)
<223> OTHER INFORMATION: L-Ile, L-Lys or O-methyl-L-Thr
<220> FEATURE:
<221> NAME/KEY: MOD_RES
<222> LOCATION: (8)..(8)
<223> OTHER INFORMATION: D-Ala or L-Ala

<400> SEQUENCE: 86

Ala Arg Val Xaa Xaa His Pro Xaa
1               5

<210> SEQ ID NO 87
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: L-Ile, Gly, L-Tyr
<220> FEATURE:
<221> NAME/KEY: MOD_RES
<222> LOCATION: (5)..(5)
<223> OTHER INFORMATION: L-Val, L-Ile, L-Glu
<220> FEATURE:
<221> NAME/KEY: MOD_RES
<222> LOCATION: (8)..(8)
<223> OTHER INFORMATION: L-Ile, L-Gly, or L-Ala

<400> SEQUENCE: 87

Xaa Arg Val Xaa Xaa His Pro Xaa
1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: L-Tyr, 3-hydroxy-L-Tyr, 3-fluoro-L-Tyr,
      2,6-difluoro-L-Tyr, 3-nitro-L-Tyr, 3,5-dinitro-L-Tyr or
      3-chloro-L-Tyr
<220> FEATURE:
<221> NAME/KEY: MOD_RES
<222> LOCATION: (5)..(5)
<223> OTHER INFORMATION: L-Val or L-Ile
<220> FEATURE:
<221> NAME/KEY: MOD_RES
<222> LOCATION: (8)..(8)
<223> OTHER INFORMATION: D-Ala

<400> SEQUENCE: 88

Xaa Arg Val Xaa Xaa His Pro Xaa
1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (4)..(4)
<223> OTHER INFORMATION: L-Tyr, 3-fluoro-L-Tyr or 3-chloro-L-Tyr
<220> FEATURE:
<221> NAME/KEY: MOD_RES
<222> LOCATION: (5)..(5)
<223> OTHER INFORMATION: O-methyl-Thr
<220> FEATURE:
<221> NAME/KEY: MOD_RES
```

```
<222> LOCATION: (8)..(8)
<223> OTHER INFORMATION: D-Ala

<400> SEQUENCE: 89

Xaa Arg Val Xaa Thr His Pro Xaa
1               5
```

US 8,993,511 B2

β-ARRESTIN EFFECTORS AND COMPOSITIONS AND METHODS OF USE THEREOF

RELATED APPLICATIONS

This application is a continuation of U.S. patent application Ser. No. 13/926,766, filed Jun. 25, 2013, allowed, which is a division of U.S. patent application Ser. No. 12/647,810, filed Dec. 28, 2009, now issued as U.S. Pat. No. 8,486,885 on Jul. 16, 2013, which claims priority from U.S. Provisional Patent Application No. 61/141,126, filed on Dec. 29, 2008, each of which is incorporated herein by reference in its entirety.

FIELD OF THE INVENTION

This application relates to a family of compounds acting as β-arrestin effectors. Such compounds may provide significant therapeutic benefit in the treatment of cardiovascular diseases, such as acute heart failure or acute hypertensive crisis.

BACKGROUND

Drugs targeting GPCRs have been developed based on a signaling paradigm in which stimulation of the receptor by an agonist (e.g., angiotensin II) leads to activation of a heterotrimeric "G protein", which then leads to second messenger/down-stream signaling (e.g., via diacylglycerol, inositoltriphosphate, calcium, etc. . . . ) and changes in physiological function (e.g., blood pressure and fluid homeostasis). There is a need for additional drugs that target GPCRs for treatment of pathology associated with blood pressure and fluid homeostasis.

The foregoing description of related art is not intended in any way as an admission that any of the documents described therein, including pending U.S. patent applications, are prior art to the present invention. Moreover, the description herein of any disadvantages associated with the described products, methods, and/or apparatus, is not intended to limit the invention. Indeed, aspects of the invention may include certain features of the described products, methods, and/or apparatus without suffering from their described disadvantages.

SUMMARY OF THE INVENTION

According to some embodiments, the present invention provides for novel β-arrestin effectors having the structure:
Xx-Yy-Val-Ww-Zz-Aa-Bb-Cc,
In the structure above, variables Aa, Bb, Cc, Ww, Xx, Yy, and Zz can be selected from the respective groups of chemical or biological moieties later described in the detailed description. β-arrestin effector derivatives and mimetics are also provided. Also provided are processes for preparing the compounds of the invention.

According to some embodiments, the present invention provides for novel β-arrestin effectors having the structure:
Xx-Arg-Val-Ww-Zz-His-Pro-Cc;
or pharmaceutically acceptable salt, solvate, or hydrate thereof. In the structure above, variables Cc, Ww, Xx, and Zz can be selected from the respective groups of chemical or biological moieties later described in the detailed description. β-arrestin effector derivatives and mimetics are also provided. Also provided are processes for preparing the compounds of the invention.

According to some embodiments, the compounds of the present invention comprise the following formula:
Sar-Arg-Val-Ww-Zz-His-Pro-Cc
or pharmaceutically acceptable salt, solvate, or hydrate thereof. In the structure above, variables Cc, Ww, and Zz can be selected from the respective groups of chemical or biological moieties later described in the detailed description. β-arrestin effector derivatives and mimetics are also provided. Also provided are processes for preparing the compounds of the invention.

According to some embodiments, the compounds of the present invention comprise the following formula:
Sar-Arg-Val-Ww-OMTh-His-Pro-Cc,
or pharmaceutically acceptable salt, solvate, or hydrate thereof. In the structure above, variables Cc, and Ww can be selected from the respective groups of chemical or biological moieties later described in the detailed description. β-arrestin effector derivatives and mimetics are also provided. Also provided are processes for preparing the compounds of the invention.

According to some embodiments the composition of the invention comprises a peptide or peptide mimetic selected from the group consisting of
a) a peptide or peptide mimetic comprising the sequence of Xx-Yy-Val-Ww-Zz-Aa-Bb-Cc,
wherein Xx is selected from the group consisting of null, sarcosine, N-methyl-L-alanine, N-methyl-D-alanine, N,N-dimethylglycine, L-aspartic acid, D-aspartic acid, L-glutamic acid, D-glutamic acid, N-methyl-L-aspartic acid, N-methyl-L-glutamic acid, pyrrolid-1-ylacetic acid, and morpholin-4-ylacetic acid;
Yy is selected from the group consisting of L-arginine, and L-lysine;
Ww is selected from the group consisting of L-isoleucine, glycine, L-tyrosine, O-methyl-L-tyrosine, L-valine, L-phenylalanine, 3-hydroxy-L-tyrosine, 2,6-dimethyl-L-tyrosine, 3-fluoro-L-tyrosine, 4-fluorophenyl-L-analine, 2,6-difluoro-L-tyrosine, 3-nitro-L-tyrosine, 3,5-dinitro-L-tyrosine, 3,5-dibromo-L-tyrosine, 3-chloro-L-tyrosine, O-allyl-L-tyrosine, and 3,5-diiodo-L-tyrosine;
Zz is selected from the group consisting of L-isoleucine, L-valine, L-tyrosine, L-glutamic acid, L-phenylalanine, L-histidine, L-lysine, L-arginine, O-methyl-L-threonine, D-alanine, and L-norvaline;
Aa is selected from the group consisting of L-histidine, L-histidine-amide, and L-lysine;
Bb is selected from the group consisting of L-proline, L-proline-amide, D-proline, and D-proline-amide; and
Cc is selected from the group consisting of null, L-isoleucine, L-isoleucine-amide, glycine, glycine-amide, L-alanine, L-alanine-amide, D-alanine, D-phenylalanine, L-norvaline;
provided that when Xx is L-Aspartic acid, Cc is not L-phenylalanine;
when Xx is sarcosine, Cc is not L-isoleucine; when Ww is glycine, Cc is not glycine; when Xx is sarcosine, and Zz is L-valine, Cc is not L-alanine; and when Xx is sarcosine, Ww is a L-tyrosine, and Zz is L-isoleucine, Cc is not L-alanine;
b) a peptide or peptide mimetic wherein the members of the sequence of the peptide or peptide mimetic maintain their relative positions as they appear in the sequence described in (a), wherein spacers of between 1 and 3 amino acids or amino acid analogues are inserted between one or more of the amino acids or amino acid analogues as described in (a) and wherein the total length of the peptide or peptide mimetic is between 6 and 25 amino acids and/or amino acid analogues; and c) a peptide or peptide mimetic that is at least 70% identical to the peptide or peptide mimetics described in (a).

According to other embodiments, the compositions of the invention comprise a peptide or peptide mimetic selected from the group consisting of a) a peptide or peptide mimetic comprising the sequence of Xx-Arg-Val-Ww-Zz-His-Pro-Cc, wherein Xx is selected from the group consisting of sarcosine, N-methyl-L-alanine, N-methyl-D-alanine, N,N-dimethylglycine, L-aspartic acid, D-aspartic acid, L-glutamic acid, D-glutamic acid, N-methyl-L-aspartic acid, N-methyl-L-glutamic acid, pyrrolid-1-ylacetic acid, and morpholin-4-ylacetic acid;

Ww is selected from the group consisting of L-isoleucine, glycine, L-tyrosine, O-methyl-L-tyrosine, L-valine, L-phenylalanine, 3-hydroxy-L-tyrosine, 2,6-dimethyl-L-tyrosine, 3-fluoro-L-tyrosine, 4-fluorophenyl-L-analine, 2,6-difluoro-L-tyrosine, 3-nitro-L-tyrosine, 3,5-dinitro-L-tyrosine, 3,5-dibromo-L-tyrosine, 3-chloro-L-tyrosine, O-allyl-L-tyrosine, and 3,5-diiodo-L-tyrosine;

Zz is selected from the group consisting of L-isoleucine, L-valine, L-tyrosine, L-glutamic acid, L-phenylalanine, L-histidine, L-lysine, L-arginine, O-methyl-L-threonine, D-alanine, and L-norvaline; and Cc is selected from the group consisting of L-isoleucine, L-isoleucine-amide, glycine, glycine-amide, L-alanine, L-alanine-amide, D-alanine, D-phenylalanine, and L-norvaline;

provided that when Xx is L-Aspartic acid, Cc is not L-phenylalanine; when Xx is sarcosine, Cc is not L-isoleucine; when Ww is glycine, Cc is not glycine; when Xx is sarcosine, and Zz is L-valine, Cc is not L-alanine; and when Xx is sarcosine, Ww is a L-tyrosine, and Zz is L-isoleucine, Cc is not L-alanine;

b) a peptide or peptide mimetic wherein the members of the sequence of the peptide or peptide mimetic maintain their relative positions as they appear in the sequence described in (a), wherein spacers of between 1 and 3 amino acids or amino acid analogues are inserted between one or more of the amino acids or amino acid analogues as described in (a) and wherein the total length of the peptide or peptide mimetic is between 8 and 25 amino acids and/or amino acid analogues; and c) a peptide or peptide mimetic that is at least 70% identical to the peptide or peptide mimetics described in (a).

According to other embodiments, the compositions of the invention comprise a peptide or peptide mimetic selected from the group consisting of a) a peptide or peptide mimetic comprising the sequence of Sar-Arg-Val-Ww-Zz-His-Pro-Cc, wherein Ww is selected from the group consisting of L-tyrosine, 3-hydroxy-L-tyrosine, 3-fluoro-L-tyrosine, 2,6-difluoro-L-tyrosine, 3-nitro-L-tyrosine, 3,5-dinitro-L-tyrosine, and 3-chloro-L-tyrosine;

Zz is selected from the group consisting of L-isoleucine, L-lysine, and O-Methyl-L-threonine; and Cc is selected from the group consisting of D-alanine, and L-alanine provided that when Xx is sarcosine, Ww is a L-tyrosine, and Zz is L-isoleucine, Cc is not L-alanine;

b) a peptide or peptide mimetic wherein the members of the sequence of the peptide or peptide mimetic maintain their relative positions as they appear in the sequence described in (a), wherein spacers of between 1 and 3 amino acids or amino acid analogues are inserted between one or more of the amino acids or amino acid analogues as described in (a) and wherein the total length of the peptide or peptide mimetic is between 8 and 25 amino acids and/or amino acid analogues; and c) a peptide or peptide mimetic that is at least 70% identical to the peptide or peptide mimetics described in (a).

In more specific embodiments, Ww is selected from the group consisting of L-tyrosine and 3-hydroxy-L-tyrosine; and Zz is selected from the group consisting of L-isoleucine and L-lysine. Optionally, the peptide or peptide mimetic comprises the sequence of SEQ ID NO:23, 27 or 67.

According to other embodiments, the compositions of the invention comprise a peptide or peptide mimetic selected from the group consisting of a) a peptide or peptide mimetic comprising the sequence of Sar-Arg-Val-Ww-OMTh-His-Pro-Cc, wherein Ww is selected from the group consisting of L-tyrosine, 3-hydroxy-L-tyrosine; 3-fluoro-L-tyrosine, and 3-chloro-L-tyrosine; and Cc is selected from the group consisting of D-alanine and L-alanine;

b) a peptide or peptide mimetic wherein the members of the sequence of the peptide or peptide mimetic maintain their relative positions as they appear in the sequence described in (a), wherein spacers of between 1 and 3 amino acids or amino acid analogues are inserted between one or more of the amino acids or amino acid analogues as described in (a) and wherein the total length of the peptide or peptide mimetic is between 8 and 25 amino acids and/or amino acid analogues; and c) a peptide or peptide mimetic that is at least 70% identical to the peptide or peptide mimetics described in (a).

In more specific embodiments, Ww is selected from the group consisting of 3-hydroxy-L-tyrosine; 3-fluoro-L-tyrosine, and 3-chloro-L-tyrosine; and Cc is L-alanine. Optionally, the peptide or peptide mimetic comprises the sequence of SEQ ID NO:77, 78 or 79.

According to other embodiments, the compositions of the invention comprise a peptide or peptide mimetic selected from the group consisting of a) a peptide or peptide mimetic comprising the sequence of Sar-Arg-Val-Ww-Tyr-His-Pro-NH$_2$, wherein Ww is selected from the group consisting of L-tyrosine, 3-hydroxy-L-tyrosine, 3-fluoro-L-tyrosine, 2,6-difluoro-L-tyrosine, 3-nitro-L-tyrosine, 3,5-dinitro-L-tyrosine, and 3-chloro-L-tyrosine;

b) a peptide or peptide mimetic wherein the members of the sequence of the peptide or peptide mimetic maintain their relative positions as they appear in the sequence described in (a), wherein spacers of between 1 and 3 amino acids or amino acid analogues are inserted between one or more of the amino acids or amino acid analogues as described in (a) and wherein the total length of the peptide or peptide mimetic is between 7 and 25 amino acids and/or amino acid analogues; and c) a peptide or peptide mimetic that is at least 70% identical to the peptide or peptide mimetics described in (a).

Optionally, the peptide or peptide mimetic comprises the sequence of SEQ ID NO:26.

According to other embodiments, the compositions of the invention comprise a peptide or peptide mimetic selected from the group consisting of a) a peptide or peptide mimetic comprising the sequence of NMAla-Arg-Val-Ww-Zz-His-Pro-Cc, wherein Ww is selected from the group consisting of L-tyrosine, 3-hydroxy-L-tyrosine, 3-fluoro-L-tyrosine, 2,6-difluoro-L-tyrosine, 3-nitro-L-tyrosine, 3,5-dinitro-L-tyrosine, and 3-chloro-L-tyrosine;

Zz is selected from the group consisting of L-isoleucine, L-lysine, and O-Methyl-L-threonine;

and Cc is selected from the group consisting of D-alanine, and L-alanine;

b) a peptide or peptide mimetic wherein the members of the sequence of the peptide or peptide mimetic maintain their relative positions as they appear in the sequence described in (a), wherein spacers of between 1 and 3 amino acids or amino acid analogues are inserted between one or more of the amino acids or amino acid analogues as described in (a) and wherein the total length of the peptide or peptide mimetic is between 8 and 25 amino acids and/or amino acid analogues; and c) a peptide or peptide mimetic that is at least 70% identical to the peptide or peptide mimetics described in (a).

In more specific embodiments, Ww is L-tyrosine, Zz is L-isoleucine, and/or Cc is L-alanine. Optionally, the peptide or peptide mimetic comprises the sequence of SEQ ID NO:34.

Optionally, any of the above described compositions of the invention are cyclic, dimerized and/or trimerized.

According to other embodiments, the compositions of the invention comprise an angiotensin 2 type 1 receptor (AT1R) β-arrestin biased ligand. In specific embodiments, the ligand has a lower half maximal effective concentration for recruiting β-arrestin-2 to an angiotensin 2 type 1 receptor than for IP1 accumulation. In more specific embodiments, the half maximal effective concentration for recruiting β-arrestin-2 to an angiotensin 2 type 1 receptor of the ligand is ten times lower than that for IP1 accumulation of the ligand. In more specific embodiments, the ligand is a composition comprising a peptide or peptide mimetic selected from the group consisting of a) a peptide or peptide mimetic comprising the sequence of Xx-Yy-Val-Ww-Zz-Aa-Bb-Cc, wherein Xx is selected from the group consisting of null, sarcosine, N-methyl-L-alanine, N-methyl-D-alanine, N,N-dimethylglycine, L-aspartic acid, D-aspartic acid, L-glutamic acid, D-glutamic acid, N-methyl-L-aspartic acid, N-methyl-L-glutamic acid, pyrrolid-1-ylacetic acid, and morpholin-4-ylacetic acid;

Yy is selected from the group consisting of L-arginine, and L-lysine;

Ww is selected from the group consisting of L-isoleucine, glycine, L-tyrosine, O-methyl-L-tyrosine, L-valine, L-phenylalanine, 3-hydroxy-L-tyrosine, 2,6-dimethyl-L-tyrosine, 3-fluoro-L-tyrosine, 4-fluorophenyl-L-analine, 2,6-difluoro-L-tyrosine, 3-nitro-L-tyrosine, 3,5-dinitro-L-tyrosine, 3,5-dibromo-L-tyrosine, 3-chloro-L-tyrosine, O-allyl-L-tyrosine, and 3,5-diiodo-L-tyrosine;

Zz is selected from the group consisting of L-isoleucine, L-valine, L-tyrosine, L-glutamic acid, L-phenylalanine, L-histidine, L-lysine, L-arginine, O-methyl-L-threonine, D-alanine, and L-norvaline;

Aa is selected from the group consisting of L-histidine, L-histidine-amide, and L-lysine;

Bb is selected from the group consisting of L-proline, L-proline-amide, D-proline, and D-proline-amide; and Cc is selected from the group consisting of null, L-isoleucine, L-isoleucine-amide, glycine, glycine-amide, L-alanine, L-alanine-amide, D-alanine, D-phenylalanine, L-norvaline;

provided that when Xx is L-Aspartic acid, Cc is not L-phenylalanine; when Xx is sarcosine, Cc is not L-isoleucine; when Ww is glycine, Cc is not glycine; when Xx is sarcosine, and Zz is L-valine, Cc is not L-alanine; and when Xx is sarcosine, Ww is a L-tyrosine, and Zz is L-isoleucine, Cc is not L-alanine;

b) a peptide or peptide mimetic wherein the members of the sequence of the peptide or peptide mimetic maintain their relative positions as they appear in the sequence described in (a), wherein spacers of between 1 and 3 amino acids or amino acid analogues are inserted between one or more of the amino acids or amino acid analogues as described in (a) and wherein the total length of the peptide or peptide mimetic is between 6 and 25 amino acids and/or amino acid analogues; and c) a peptide or peptide mimetic that is at least 70% identical to the peptide or peptide mimetics described in (a).

In more specific embodiments, the ligand is a composition comprising a peptide or peptide mimetic selected from the group consisting of a) a peptide or peptide mimetic comprising the sequence of Xx-Arg-Val-Ww-Zz-His-Pro-Cc, wherein Xx is selected from the group consisting of sarcosine, N-methyl-L-alanine, N-methyl-D-alanine, N,N-dimethylglycine, L-aspartic acid, D-aspartic acid, L-glutamic acid, D-glutamic acid, N-methyl-L-aspartic acid, N-methyl-L-glutamic acid, pyrrolid-1-ylacetic acid, and morpholin-4-ylacetic acid;

Ww is selected from the group consisting of L-isoleucine, glycine, L-tyrosine, O-methyl-L-tyrosine, L-valine, L-phenylalanine, 3-hydroxy-L-tyrosine, 2,6-dimethyl-L-tyrosine, 3-fluoro-L-tyrosine, 4-fluorophenyl-L-analine, 2,6-difluoro-L-tyrosine, 3-nitro-L-tyrosine, 3,5-dinitro-L-tyrosine, 3,5-dibromo-L-tyrosine, 3-chloro-L-tyrosine, O-allyl-L-tyrosine, and 3,5-diiodo-L-tyrosine;

Zz is selected from the group consisting of L-isoleucine, L-valine, L-tyrosine, L-glutamic acid, L-phenylalanine, L-histidine, L-lysine, L-arginine, O-methyl-L-threonine, D-alanine, and L-norvaline; and Cc is selected from the group consisting of L-isoleucine, L-isoleucine-amide, glycine, glycine-amide, L-alanine, L-alanine-amide, D-alanine, D-phenylalanine, and L-norvaline;

provided that when Xx is L-Aspartic acid, Cc is not L-phenylalanine; when Xx is sarcosine, Cc is not L-isoleucine; when Ww is glycine, Cc is not glycine; when Xx is sarcosine, and Zz is L-valine, Cc is not L-alanine; and when Xx is sarcosine, Ww is a L-tyrosine, and Zz is L-isoleucine, Cc is not L-alanine;

b) a peptide or peptide mimetic wherein the members of the sequence of the peptide or peptide mimetic maintain their relative positions as they appear in the sequence described in (a), wherein spacers of between 1 and 3 amino acids or amino acid analogues are inserted between one or more of the amino acids or amino acid analogues as described in (a) and wherein the total length of the peptide or peptide mimetic is between 8 and 25 amino acids and/or amino acid analogues; and c) a peptide or peptide mimetic that is at least 70% identical to the peptide or peptide mimetics described in (a).

According to other embodiments, the invention provides a pharmaceutical composition comprising one or more of the above described peptides or peptide mimetics and a pharmaceutically acceptable carrier. In specific embodiments, the pharmaceutically acceptable carrier is pure sterile water, phosphate buffered saline or an aqueous glucose, solution.

According to other embodiments, the invention provides a method of treating cardiovascular disorders comprising: administering to a subject in need thereof a therapeutically effective amount of one or more compositions described above. In specific embodiments, the cardiovascular disorder is selected from the groups consisting of chronic hypertension, hypertensive crisis, acute congestive heart failure, angina, acute myocardial infarction, left ventricular failure, cerebrovascular insufficiency, intracranial haemorrhage, heart failure, acute decompensated heart failure, essential hypertension, post-operative hypertension, hypertensive heart disease, hypertensive renal disease, renovascular hypertension, malignant hypertension, post-renal transplant patient stabilization, dilated cardiomyopathy, myocarditis, post-cardiac transplant patient stabilization, disorders associated with post-stent management, neurogenic hypertension, pre-eclampsia, abdominal aortic aneurysm, and any cardiovascular disorder with a hemodynamic component. In more specific embodiments, the cardiovascular disorder is an acute cardiovascular disorder. In other specific embodiments, the acute cardiovascular disorder is acute hypertensive crisis, toxemia of pregnancy, acute myocardial infarction, acute congestive heart failure, acute ischaemic heart disease, pulmonary hypertension, post-operative hypertension, migraine, retinopathy and post-operative cardiac/valve surgery.

According to other embodiments, the invention also provides a method of treating viral infectious disease linked to AT1R comprising: administering to a subject in need thereof a therapeutically effective amount of one or more compositions described above. In specific embodiments, the one or more compositions are administered by intravenous injection.

According to other embodiments, the invention also provides a method of treating cardiovascular disorders comprising: administering to a subject in need thereof a therapeutically effective amount of one or more a peptides or peptide mimetics comprising the sequence of
  Sar-Arg-Val-Ww-Zz-His-Pro-Cc,
    wherein Ww is selected from the group consisting of L-isoleucine, glycine, and L-tyrosine;
    Zz is selected from the group consisting of L-valine, L-isoleucine and L-glutamate; and
    Cc is selected from the group consisting of L-isoleucine, glycine, and L-alanine.

In specific embodiments, the one or more peptides or peptide mimetics are selected from the group consisting of SEQ ID NOs: 3, 5, 7, 9, 11, 14, and 16. in more specific embodiments, the cardiovascular disorder is selected from the groups consisting of chronic hypertension, hypertensive crisis, acute congestive heart failure, angina, acute myocardial infarction, left ventricular failure, cerebrovascular insufficiency, intracranial haemorrhage, heart failure, acute decompensated heart failure, essential hypertension, post-operative hypertension, hypertensive heart disease, hypertensive renal disease, renovascular hypertension, malignant hypertension, post-renal transplant patient stabilization, dilated cardiomyopathy, myocarditis, post-cardiac transplant patient stabilization, disorders associated with post-stent management, neurogenic hypertension, pre-eclampsia, abdominal aortic aneurysm, and any cardiovascular disorder with a hemodynamic component. In other specific embodiments, the cardiovascular disorder is an acute cardiovascular disorder. In other specific embodiments, the acute cardiovascular disorder is acute hypertensive crisis, toxemia of pregnancy, acute myocardial infarction, acute congestive heart failure, acute ischaemic heart disease, pulmonary hypertension, post-operative hypertension, migraine, retinopathy and post-operative cardiac/valve surgery.

According to other embodiments, the invention also provides a method of treating viral infectious disease linked to AT1R comprising: administering to a subject in need thereof a therapeutically effective amount of one or more a peptides or peptide mimetics comprising the sequence of
  Sar-Arg-Val-Ww-Zz-His-Pro-Cc,
    wherein Ww is selected from the group consisting of L-isoleucine, glycine, and L-tyrosine;
    Zz is selected from the group consisting of L-valine, L-isoleucine and L-glutamate; and
    Cc is selected from the group consisting of L-isoleucine, glycine, and L-alanine.

In specific embodiments, the one or more peptides or peptide mimetics are selected from the group consisting of SEQ ID NOs: 3, 5, 7, 9, 11, 14, and 16. According to other embodiments, the invention also provides a method of agonizing β-arrestin comprising: administering to a subject in need thereof an effective amount of one or more compositions described above.

According to some embodiments, the present invention extends to a pharmaceutical composition comprising a compound of the invention and a pharmaceutically acceptable carrier. Naturally, the compounds of the present invention can be employed in any form, such as a solid or solution (e.g., aqueous solution) as is described further below. The compound, for example, can be obtained and employed in a lyophilized form alone or with suitable additives.

Also provided are methods for treating cardiovascular disorders. Such a method would comprise administering a therapeutically effective amount of one or more compounds of the present invention to a subject in need thereof.

DETAILED DESCRIPTION OF THE PREFERRED EMBODIMENTS

Before the present proteins, nucleotide sequences, peptides, etc., and methods are described, it is understood that this invention is not limited to the particular methodology, protocols, cell lines, vectors, and reagents described, as these may vary. It also is to be understood that the terminology used herein is for the purpose of describing particular embodiments only, and is not intended to limit the scope of the present invention which will be limited only by the appended claims.

This application describes a family of compounds, β-arrestin effectors, with a unique profile. The compounds of the present invention act as agonists of β-arrestin/GRK-mediated signal transduction via the AT1 angiotensin receptor. Thus, these compounds stimulate signaling pathways that provide significant therapeutic benefit in the treatment of cardiovascular diseases such as acute heart failure or acute hypertensive crisis.

According to some embodiments, the compounds of the present invention comprise the following formula:
  Xx-Yy-Val-Ww-Zz-Aa-Bb-Cc,
  wherein Xx is null, sarcosine, N-methyl-L-alanine, N-methyl-D-alanine, N,N-dimethylglycine, L-aspartic acid, D-aspartic acid, L-glutamic acid, D-glutamic acid, N-methyl-L-aspartic acid, N-methyl-L-glutamic acid, pyrrolid-1-ylacetic acid, or morpholin-4-ylacetic acid; Yy is L-arginine, or L-lysine; Ww is L-isoleucine, glycine, L-tyrosine, O-methyl-L-tyrosine, L-valine, L-phenylalanine, 3-hydroxy-L-tyrosine, 2,6-dimethyl-L-tyrosine, 3-fluoro-L-tyrosine, 4-fluorophenyl-L-analine, 2,6-difluoro-L-tyrosine, 3-nitro-L- tyrosine, 3,5-dinitro-L-tyrosine, 3,5-dibromo-L-tyrosine, 3-chloro-L-tyrosine, O-allyl-L-tyrosine, or 3,5-diiodo-L-tyrosine; Zz is L-isoleucine, L-valine, L-tyrosine, L-glutamic acid, L-phenylalanine, L-histidine, L-lysine, L-arginine, O-methyl-L-threonine, D-alanine, or L-norvaline; Aa is L-histidine, L-histidine-amide, or L-lysine; Bb is L-proline, L-proline-amide, D-proline, D-proline-amide and Cc is null, L-isoleucine, L-isoleucine-amide, glycine, glycine-amide, L-alanine, L-alanine-amide, D-alanine, D-phenylalanine, L-norvaline;

provided that when Xx is L-aspartic acid, Cc is not L-phenylalanine;

provided that when Xx is sarcosine, Cc is not L-isoleucine;

provided that when Ww is glycine, Cc is not glycine;

provided that when Xx is sarcosine, and Zz is L-valine, Cc is not L-alanine;

provided that when Xx is sarcosine, Ww is a L-tyrosine, and Zz is L-isoleucine, Cc is not L-alanine;

According to some embodiments, the compounds of the present invention comprise the following formula:

Xx-Arg-Val-Ww-Zz-His-Pro-Cc, wherein Xx is sarcosine, N-methyl-L-alanine, N-methyl-D-alanine, N,N-dimethylglycine, L-aspartic acid, D-aspartic acid, L-glutamic acid, D-glutamic acid, N-methyl-L-aspartic acid, N-methyl-L-glutamic acid, pyrrolid-1-ylacetic acid, or morpholin-4-ylacetic acid; Ww is L-isoleucine, glycine, L-tyrosine, O-methyl-L-tyrosine, L-valine, L-phenylalanine, 3-hydroxy-L-tyrosine, 2,6-dimethyl-L-tyrosine, 3-fluoro-L-tyrosine, 4-fluorophenyl-L-analine, 2,6-difluoro-L-tyrosine, 3-nitro-L-tyrosine, 3,5-dinitro-L-tyrosine, 3,5-dibromo-L-tyrosine, 3-chloro-L-tyrosine, O-allyl-L-tyrosine, or 3,5-diiodo-L-tyrosine; Zz is L-isoleucine, L-valine, L-tyrosine, L-glutamic acid, L-phenylalanine, L-histidine, L-lysine, L-arginine, O-methyl-L-threonine, D-alanine, or L-norvaline; and Cc is L-isoleucine, L-isoleucine-amide, glycine, glycine-amide, L-alanine, L-alanine-amide, D-alanine, D-phenylalanine, L-norvaline.

provided that when Xx is L-aspartic acid, Cc is not L-phenylalanine;

provided that when Xx is sarcosine, Cc is not L-isoleucine;

provided that when Ww is glycine, Cc is not glycine;

provided that when Xx is sarcosine, and Zz is L-valine, Cc is not L-alanine;

provided that when Xx is sarcosine, Ww is a L-tyrosine, and Zz is L-isoleucine, Cc is not L-alanine;

According to some embodiments, the compounds of the present invention comprise the following formula:

Sar-Arg-Val-Ww-Zz-His-Pro-Cc, wherein Ww is L-tyrosine, 3-hydroxy-L-tyrosine, 3-fluoro-L-tyrosine, 2,6-difluoro-L-tyrosine, 3-nitro-L-tyrosine, 3,5-dinitro-L-tyrosine, 3-chloro-L-tyrosine; Zz is L-valine or L-isoleucine; and Cc is D-alanine.

According to some embodiments, the compounds of the present invention comprise the following formula:

Sar-Arg-Val-Ww-OMTh-His-Pro-Cc, wherein Ww is L-tyrosine, 3-fluoro-L-tyrosine, 3-chloro-L-tyrosine; and Cc is D-alanine or L-alanine.

The definition of some of the abbreviations used in the present invention is given below:

| Abbreviation | Chemical name of amino acid or its analog | Structure of amino acid or its analog |
|---|---|---|
| Ala | L-Alanine | |
| D-Ala | D-Alanine | |
| NMAla | N-Methyl-L-alanine | |
| NM-D-Ala | N-Methyl-D-alanine | |
| Me2G | N,N-dimethyl-glycine | |
| Asp | L-Aspartic acid | |
| D-Asp | D-Aspartic acid | |
| Glu | L-Glutamic acid | |
| D-Glu | D-Glutamic acid | |

-continued

| Abbreviation | Chemical name of amino acid or its analog | Structure of amino acid or its analog |
|---|---|---|
| N-Me-Asp | N-Methyl-L-aspartic acid | |
| N-Me-Glu | N-Methyl-L-glutamic acid | |
| Sar | Sarcosine | |
| MMM | Pyrrolid-l-ylacetic acid | |
| NNN | Morpholin-4-ylacetic acid | |
| Arg | L-Arginine | |
| Lys | L-Lysine | |
| ILe | L-Isoleucine | |

-continued

| Abbreviation | Chemical name of amino acid or its analog | Structure of amino acid or its analog |
|---|---|---|
| Gly | Glycine | |
| Tyr | L-Tyrosine | |
| OMTyr | O-Methyl-L-tyrosine | |
| Val | L-Valine | |
| Phe | L-Phenylalanine | |
| D-Phe | D-Phenylalanine | |
| AAA | 3-Hydroxy-L-tyrosine | |

| Abbreviation | Chemical name of amino acid or its analog | Structure of amino acid or its analog |
| --- | --- | --- |
| BBB | 2,6-Dimethyl-L-tyrosine | (structure) |
| CCC | 3-Fluoro-L-tyrosine | (structure) |
| DDD | 4-Fluorophenyl-L-alanine | (structure) |
| EEE | 2,6-Difluoro-L-tyrosine | (structure) |
| FFF | 3-Nitro-L-tyrosine | (structure) |
| GGG | 3,5-Dinitro-L-tyrosine | (structure) |
| HHH | 3,5-Dibromo-L-tyrosine | (structure) |
| III | 3-Chloro-L-tyrosine | (structure) |
| JJJ | O-Allyl-L-tyrosine | (structure) |
| OOO | 3,5-Diiodo-L-tyrosine | (structure) |
| His | L-Histidine | (structure) |
| OMTh | O-Methyl-L-threonine | (structure) |

-continued

| Abbreviation | Chemical name of amino acid or its analog | Structure of amino acid or its analog |
|---|---|---|
| NVA | L-Norvaline | |
| Pro | L-Proline | |
| D-Pro | D-Proline | |
| | L-Histidine-amide | |
| | L-Proline amide | |
| | D-Proline amide | |
| | L-Isoleucine amide | |
| | Glycine amide | |
| | L-Alanine amide | |

Cyclic forms, cyclic truncated forms, cyclic truncated dimerized forms, and cyclic truncated trimerized forms of the compounds of the above formulas may be prepared using any known method. Truncated is defined as analogs with amino acids removed from the X1 and/or X2 residues as depicted in Table 1. According to some embodiments, cyclic forms of the compounds of the above formulas may be prepared by bridging free amino and free carboxyl groups. According to some embodiments, formation of the cyclic compounds may be conducted conventionally by treatment with a dehydrating agent by means known in the art, with suitable protection if needed. According to some embodiments, the open chain (linear form) to cyclic form reaction may involve a trans to cis isomerization of the proline. According to some embodiments, the open chain (linear form) to cyclic form reaction may involve intramolecular-cyclization.

Examples of the compounds of the present invention include, but are not limited to, the compounds listed in Table 1 below.

TABLE 1

| SEQ ID NO: | $X_1$ | $X_2$ | $X_3$ | $X_4$ | $X_5$ | $X_6$ | $X_7$ | $X_8$ | |
|---|---|---|---|---|---|---|---|---|---|
| AngII | Asp | Arg | Val | Tyr | Ile | His | Pro | Phe | OH |
| 2 | Sar | Arg | Val | Ile | Ile | His | Pro | Ile | NH2 |
| 3 | Sar | Arg | Val | Ile | Val | His | Pro | Ile | OH |
| 5 | Sar | Arg | Val | Gly | Val | His | Pro | Gly | OH |
| 6 | Sar | Arg | Val | Gly | Val | His | Pro | Gly | NH2 |
| 7 | Sar | Arg | Val | Tyr | Val | His | Pro | Ala | OH |
| 8 | Sar | Arg | Val | Tyr | Val | His | Pro | Ala | NH2 |
| 9 | Sar | Arg | Val | Tyr | Ile | His | Pro | Ala | OH |
| 10 | Sar | Arg | Val | Tyr | Ile | His | Pro | Ala | NH2 |
| 11 | Sar | Arg | Val | Tyr | Val | His | Pro | Ile | OH |
| 12 | Sar | Arg | Val | Tyr | Val | His | Pro | Ile | NH2 |

TABLE 1-continued

| SEQ ID NO: | X₁ | X₂ | X₃ | X₄ | X₅ | X₆ | X₇ | X₈ |
|---|---|---|---|---|---|---|---|---|
| 13 | | Arg | Val | Tyr | Ile | His | Pro | NH2 |
| 14 | Sar | Arg | Val | Tyr | Tyr | His | Pro | Ile | OH |
| 15 | Sar | Arg | Val | Tyr | Tyr | His | Pro | Ile | NH2 |
| 16 | Sar | Arg | Val | Tyr | Glu | His | Pro | Ile | OH |
| 19 | Sar | Arg | Val | Tyr | Tyr | His | Pro | Ala | OH |
| 20 | Sar | Arg | Val | Tyr | Glu | His | Pro | Ala | OH |
| 21 | Sar | Arg | Val | Tyr | Phe | His | Pro | Ala | OH |
| 22 | Sar | Arg | Val | Tyr | His | His | Pro | Ala | OH |
| 23 | Sar | Arg | Val | Tyr | Lys | His | Pro | Ala | OH |
| 24 | Sar | Arg | Val | Tyr | Arg | His | Pro | Ala | OH |
| 25 | Asp | Arg | Val | Tyr | Ile | His | Pro | Ala | OH |
| 26 | Sar | Arg | Val | Tyr | Tyr | His | Pro | NH2 |
| 27 | Sar | Arg | Val | Tyr | Ile | His | Pro | D-Ala | OH |
| 28 | Sar | Arg | Val | Tyr | Tyr | His | Pro | D-Phe | OH |
| 29 | Sar | Arg | Val | OMTyr | Ile | His | Pro | Ala | OH |
| 30 | Sar | Arg | Val | Tyr | OMTh | His | Pro | Ala | OH |
| 31 | Me2G | Arg | Val | Tyr | Val | His | Pro | Ala | OH |
| 32 | Me2G | Arg | Val | Tyr | Ile | His | Pro | Ala | OH |
| 33 | NMAla | Arg | Val | Tyr | Val | His | Pro | Ala | OH |
| 34 | NMAla | Arg | Val | Tyr | Ile | His | Pro | Ala | OH |
| 35 | Sar | Arg | Val | Tyr | Ile | His | Pro | NVA | OH |
| 36 | Cyclo(Arg-Val-Tyr-Ile-His-Pro-Arg-Val-Tyr-Ile-His-Pro-Arg-Val-Tyr-Ile-His-Pro) | | | | | | | | |
| 37 | Cyclo(Phe-Val-Tyr-Ile-His-Pro-Phe-Val-Tyr-Ile-His-Pro-Phe-Val-Tyr-Ile-His-Pro) | | | | | | | | |
| 38 | Cyclo(Val-Tyr-Ile-His-Pro-Phe) | | | | | | | | |
| 40 | Sar | Arg | Val | Tyr | Glu | His | Pro | NH2 |
| 41 | Sar | Arg | Val | Tyr | Phe | His | Pro | NH2 |
| 42 | Sar | Arg | Val | Tyr | His | His | Pro | NH2 |
| 43 | Sar | Arg | Val | Tyr | Lys | His | Pro | NH2 |
| 44 | NMAla | Arg | Val | Tyr | Ile | His | Pro | D-Ala | OH |
| 45 | Sar | Arg | Val | Tyr | Arg | His | Pro | NH2 |
| 46 | NMAla | Arg | Val | Tyr | Ile | His | Pro | D-Ala | OH |
| 47 | NM-D-Ala | Arg | Val | Tyr | Ile | His | Pro | Ala | OH |
| 48 | Sar | Arg | Val | Phe | Ile | His | Pro | D-Ala | OH |
| 49 | Sar | Lys | Val | Tyr | Ile | His | Pro | D-Ala | OH |
| 50 | Sar | Arg | Val | Tyr | Ile | Lys | Pro | D-Ala | OH |
| 51 | Sar | Arg | Val | Tyr | Ile | His | D-Pro | NH2 |

TABLE 1-continued

| SEQ ID NO: | X₁ | X₂ | X₃ | X₄ | X₅ | X₆ | X₇ | X₈ | |
|---|---|---|---|---|---|---|---|---|---|
| 52 | Sar | Arg | Val | Tyr | Tyr | His | Pro | OH | |
| 53 | Sar | Arg | Val | Tyr | D-Ala | His | Pro | NH2 | |
| 54 | Sar | Arg | Val | Tyr | Val | His | Pro | OH | |
| 55 | Sar | Arg | Val | Tyr | Val | His | NH2 | | |
| 56 | Asp | Arg | Val | Tyr | Ile | His | Pro | Gly | OH |
| 57 | Asp | Arg | Val | Tyr | Tyr | His | Pro | NH2 | |
| 58 | D-Asp | Arg | Val | Tyr | Tyr | His | Pro | NH2 | |
| 59 | Glu | Arg | Val | Tyr | Tyr | His | Pro | NH2 | |
| 60 | D-Glu | Arg | Val | Tyr | Tyr | His | Pro | NH2 | |
| 61 | N-Me-Asp | Arg | Val | Tyr | Tyr | His | Pro | NH2 | |
| 62 | Glu | Arg | Val | Tyr | Tyr | His | Pro | NH2 | |
| 63 | Asp | Arg | Val | Tyr | Phe | His | Pro | NH2 | |
| 64 | Glu | Arg | Val | Tyr | Phe | His | Pro | NH2 | |
| 65 | N-Me-Asp | Arg | Val | Tyr | Phe | His | Pro | NH2 | |
| 66 | Glu | Arg | Val | Tyr | Phe | His | Pro | NH2 | |
| 67 | Sar | Arg | Val | AAA | Ile | His | Pro | D-Ala | OH |
| 68 | Sar | Arg | Val | BBB | Ile | His | Pro | D-Ala | OH |
| 69 | Sar | Arg | Val | CCC | Ile | His | Pro | D-Ala | OH |
| 70 | Sar | Arg | Val | DDD | Ile | His | Pro | D-Ala | OH |
| 71 | Sar | Arg | Val | EEE | Ile | His | Pro | D-Ala | OH |
| 72 | Sar | Arg | Val | FFF | Ile | His | Pro | D-Ala | OH |
| 73 | Sar | Arg | Val | GGG | Ile | His | Pro | D-Ala | OH |
| 74 | Sar | Arg | Val | HHH | Ile | His | Pro | D-Ala | OH |
| 75 | Sar | Arg | Val | III | Ile | His | Pro | D-Ala | OH |
| 76 | Sar | Arg | Val | JJJ | Ile | His | Pro | D-Ala | OH |
| 77 | Sar | Arg | Val | AAA | OMTh | His | Pro | Ala | OH |
| 78 | Sar | Arg | Val | CCC | OMTh | His | Pro | Ala | OH |
| 79 | Sar | Arg | Val | III | OMTh | His | Pro | Ala | OH |
| 80 | MMM | Arg | Val | Tyr | Ile | His | Pro | D-Ala | OH |
| 81 | NNN | Arg | Val | Tyr | Ile | His | Pro | D-Ala | OH |
| 82 | NM-D-Ala | Arg | Val | Tyr | Ile | His | Pro | D-Ala | OH |
| 83 | Sar | Arg | Val | Tyr | NVA | His | Pro | D-Ala | OH |
| 84 | Sar | Arg | Val | Tyr | OMTh | His | Pro | D-Ala | OH |
| 85 | Sar | Arg | Val | OOO | Ile | His | Pro | D-Ala | OH |

The definition of the amino acid or its analogues, please refer to the table of abbreviation.

Determining GPCR Activity

The compounds of the preferred embodiments are agonists of β-arrestin/GRK-mediated signal transduction via the AT1 angiotensin receptor. The ability of the compounds to effect G protein-mediated signaling may be measured using any assay known in the art used to detect G protein-mediated signaling or GPCR activity, or the absence of such signaling/activity. "GPCR activity" refers to the ability of a GPCR to transduce a signal. Such activity can be measured, e.g., in a heterologous cell, by coupling a GPCR (or a chimeric GPCR) to a G-protein and a downstream effector such as PLC or adenylate cyclase, and measuring increases in intracellular calcium (see, e.g., Offermans & Simon, J. Biol. Chem. 270:15175 15180 (1995)). Receptor activity can be effectively measured by recording ligand-induced changes in $[Ca^{2+}]_i$ using fluorescent $Ca^{2+}$-indicator dyes and fluorometric imaging. A "natural ligand-induced activity" as used herein, refers to activation of the GPCR by a natural ligand of the GPCR. Activity can be assessed using any number of endpoints to measure the GPCR activity. For example, activity of a GPCR may be assessed using an assay such as calcium mobilization, e.g., an Aequorin luminescence assay.

Generally, assays for testing compounds that modulate GPCR-mediated signal transduction include the determination of any parameter that is indirectly or directly under the influence of a GPCR, e.g., a functional, physical, or chemical effect. It includes ligand binding, changes in ion flux, membrane potential, current flow, transcription, G-protein binding, gene amplification, expression in cancer cells, GPCR phosphorylation or dephosphorylation, signal transduction, receptor-ligand interactions, second messenger concentrations (e.g., cAMP, cGMP, $IP_3$, DAG, or intracellular $Ca^{2+}$), in vitro, in vivo, and ex vivo and also includes other physiologic effects such as increases or decreases of neurotransmitter or hormone release; or increases in the synthesis of particular compounds, e.g., triglycerides. Such parameters can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, transcriptional activation of GPCRs; ligand binding assays; voltage, membrane potential and conductance changes; ion flux assays; changes in intracellular second messengers such as cAMP and inositol triphosphate ($IP_3$); changes in intracellular calcium levels; neurotransmitter release, and the like.

When a G protein receptor becomes active, it binds to a G protein (e.g., Gq, Gs, Gi, Go) and stimulates the binding of GTP to the G protein. The G protein then acts as a GTPase and slowly hydrolyzes the GTP to GDP, whereby the receptor, under normal conditions, becomes deactivated. G protein-mediated signaling or GPCR activity may be measured using assay systems that are capable of detecting and/or measuring GTP binding and/or hydrolysis of GTP to GDP.

Gs stimulates the enzyme adenylyl cyclase. Gi (and Go), on the other hand, inhibit this enzyme. Adenylyl cyclase catalyzes the conversion of ATP to cAMP. Thus, constitutively activated GPCRs that couple the Gs protein are associated with increased cellular levels of cAMP. On the other hand, activated GPCRs that couple the Gi (or Go) protein are associated with decreased cellular levels of cAMP. Thus, assays that detect cAMP can be utilized to determine if a candidate compound is, e.g., an inverse agonist to the receptor (i.e., such a compound would decrease the levels of cAMP). A variety of approaches known in the art for measuring cAMP can be utilized; a most preferred approach relies upon the use of anti-cAMP antibodies in an ELISA-based format. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) which then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, a constitutively activated Gs-linked receptor causes the accumulation of cAMP that then activates the gene and expression of the reporter protein. The reporter protein such as β-galactosidase or luciferase can then be detected using standard biochemical assays.

Gq and Go are associated with activation of the enzyme phospholipase C, which in turn hydrolyzes the phospholipid PIP2, releasing two intracellular messengers: diacycloglycerol (DAG) and inistol 1,4,5-triphoisphate (IP3). Increased accumulation of IP3 is associated with activation of Gq- and Go-associated receptors. Assays that detect IP3 accumulation can be utilized to determine if a candidate compound is, e.g., an inverse agonist to a Gq- or Go-associated receptor (i.e., such a compound would decrease the levels of IP3). Gq-dependent receptors can also be examined using an AP1 reporter assay in that Gq-dependent phospholipase C causes activation of genes containing AP1 elements.

Samples or assays comprising GPCRs that are treated with a potential activator, inhibitor, or modulator are compared to control samples without the inhibitor, activator, or modulator to examine the extent of inhibition. Control samples (untreated with inhibitors) are assigned a relative GPCR activity value of 100%. Inhibition of a GPCR is achieved when the GPCR activity value relative to the control is about 80%, preferably 50%, more preferably 25%. Activation of a GPCR is achieved when the GPCR activity value relative to the control (untreated with activators) is 110%, more preferably 150%, more preferably 200-500% (i.e., two to five fold higher relative to the control), more preferably 1000-3000% or higher.

The effects of the compounds upon the function of the GPCR polypeptides can be measured by examining any of the parameters described above. Any suitable physiological change that affects GPCR activity can be used to assess the influence of a compound on the GPCRs and natural ligand-mediated GPCR activity. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3 or cAMP.

For a general review of GPCR signal transduction and methods of assaying signal transduction, see, e.g., Methods in Enzymology, vols. 237 and 238 (1994) and volume 96 (1983); Bourne et al., Nature 10:349:117 27 (1991); Bourne et al., Nature 348:125 32 (1990); Pitcher et al., Annu. Rev. Biochem. 67:653 92 (1998).

Modulators of GPCR activity are tested using GPCR polypeptides as described above, either recombinant or naturally occurring. The protein can be isolated, expressed in a cell, expressed in a membrane derived from a cell, expressed in tissue or in an animal. For example, adipocytes, cells of the immune system, transformed cells, or membranes can be used to test the GPCR polypeptides described above. Modulation is tested using one of the in vitro or in vivo assays described herein. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Furthermore, ligand-binding domains of the protein of interest can be used in vitro in soluble or solid state reactions to assay for ligand binding.

Ligand binding to a GPCR, a domain, or chimeric protein can be tested in a number of formats. Binding can be performed in solution, in a bilayer membrane, attached to a solid phase, in a lipid monolayer, or in vesicles. Typically, in an assay of the invention, the binding of the natural ligand to its receptor is measured in the presence of a candidate modulator. Alternatively, the binding of the candidate modulator may be measured in the presence of the natural ligand. Often, competitive assays that measure the ability of a compound to compete with binding of the natural ligand to the receptor are used. Binding can be tested by measuring, e.g., changes in spectroscopic characteristics (e.g., fluorescence, absorbance, refractive index), hydrodynamic (e.g., shape) changes, or changes in chromatographic or solubility properties.

Receptor-G-protein interactions can also be used to assay for modulators. For example, in the absence of GTP, binding of an activator such as the natural ligand will lead to the formation of a tight complex of a G protein (all three subunits) with the receptor. This complex can be detected in a variety of ways, as noted above. Such an assay can be modified to search for inhibitors. For example, the ligand can be added to the receptor and G protein in the absence of GTP to form a tight complex Inhibitors or antagonists may be identified by looking at dissociation of the receptor-G protein complex. In the presence of GTP, release of the α subunit of the G protein from the other two G protein subunits serves as a criterion of activation.

An activated or inhibited G-protein will in turn alter the properties of downstream effectors such as proteins, enzymes, and channels. The classic examples are the activation of cGMP phosphodiesterase by transducin in the visual system, adenylate cyclase by the stimulatory G-protein, phospholipase C by Gq and other cognate G proteins, and modulation of diverse channels by Gi and other G proteins. Downstream consequences such as generation of diacyl glycerol and IP3 by phospholipase C, and in turn, for calcium mobilization, e.g., by IP3 (further discussed below) can also be examined. Thus, modulators can be evaluated for the ability to stimulate or inhibit ligand-mediated downstream effects. Candidate modulators may be assessed for the ability to inhibit calcium mobilization induced by nicotinic acid or a related compound that activates the receptor.

In other examples, the ability of a compound to inhibit GPCR activity can be determined using downstream assays such as measuring lipolysis in adipocytes, release of free fatty acids from adipose tissue, and lipoprotein lipase activity. This may be accomplished, for example, using a competition assay in which varying amounts of a compound are incubated with a GPCR.

Modulators may therefore also be identified using assays involving β-arrestin recruitment. β-arrestin serves as a regulatory protein that is distributed throughout the cytoplasm in unactivated cells. Ligand binding to an appropriate GPCR is associated with redistribution of β-arrestin from the cytoplasm to the cell surface, where it associates with the GPCR. Thus, receptor activation and the effect of candidate modulators on ligand-induced receptor activation, can be assessed by monitoring β-arrestin recruitment to the cell surface. This is frequently performed by transfecting a labeled β-arrestin fusion protein (e.g., β-arrestin-green fluorescent protein (GFP)) into cells and monitoring its distribution using confocal microscopy (see, e.g., Groarke et al., J. Biol. Chem. 274(33):23263 69 (1999)).

Receptor internalization assays may also be used to assess receptor function. Upon ligand binding, the G-protein coupled receptor—ligand complex is internalized from the plasma membrane by a clathrin-coated vesicular endocytic process; internalization motifs on the receptors bind to adaptor protein complexes and mediate the recruitment of the activated receptors into clathrin-coated pits and vesicles. Because only activated receptors are internalized, it is possible to detect ligand-receptor binding by determining the amount of internalized receptor. In one assay format, cells are transiently transfected with radiolabeled receptor and incubated for an appropriate period of time to allow for ligand binding and receptor internalization. Thereafter, surface-bound radioactivity is removed by washing with an acid solution, the cells are solubilized, and the amount of internalized radioactivity is calculated as a percentage of ligand binding. See, e.g., Vrecl et al., Mol. Endocrinol. 12:1818 29 (1988) and Conway et al., J. Cell Physiol. 189(3):341 55 (2001). In addition, receptor internalization approaches have allowed real-time optical measurements of GPCR interactions with other cellular components in living cells (see, e.g., Barak et al., Mol. Pharmacol. 51(2)177 84 (1997)). Modulators may be identified by comparing receptor internalization levels in control cells and cells contacted with candidate compounds.

Another technology that can be used to evaluate GPCR-protein interactions in living cells involves bioluminescence resonance energy transfer (BRET). A detailed discussion regarding BRET can be found in Kroeger et al., J. Biol. Chem., 276(16):12736 43 (2001).

Receptor-stimulated guanosine 5'-O-(γ-Thio)-Triphosphate ([$^{35}$S]GTPγS) binding to G-proteins may also be used as an assay for evaluating modulators of GPCRs. [$^{35}$S]GTPγS is a radiolabeled GTP analog that has a high affinity for all types of G-proteins, is available with a high specific activity and, although unstable in the unbound form, is not hydrolyzed when bound to the G-protein. Thus, it is possible to quantitatively assess ligand-bound receptor by comparing stimulated versus unstimulated [$^{35}$S]GTPγS binding utilizing, for example, a liquid scintillation counter Inhibitors of the receptor-ligand interactions would result in decreased [$^{35}$S]GTPγS binding. Descriptions of [$^{35}$S]GTPγS binding assays are provided in Traynor and Nahorski, Mol. Pharmacol. 47(4):848 54 (1995) and Bohn et al., Nature 408:720 23 (2000).

The ability of modulators to affect ligand-induced ion flux may also be determined. Ion flux may be assessed by determining changes in polarization (i.e., electrical potential) of the cell or membrane expressing a GPCR. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., New Engl. J. Med. 336:1575 1595 (1997)). Whole cell currents are conveniently determined using the standard methodology (see, e.g., Hamil et al., PFlugers. Archiv. 391:85 (1981). Other known assays include: radiolabeled ion flux assays and fluorescence assays using voltage-sensitive dyes (see, e.g., Vestergarrd-Bogind et al., J. Membrane Biol. 88:67 75 (1988); Gonzales & Tsien, Chem. Biol. 4:269 277 (1997); Daniel et al., J. Pharmacol. Meth. 25:185 193 (1991); Holevinsky et al., J. Membrane Biology 137:59 70 (1994)). Generally, the compounds to be tested are present in the range from 1 pM to 100 mM.

Preferred assays for G-protein coupled receptors include cells that are loaded with ion or voltage sensitive dyes to report receptor activity. Assays for determining activity of such receptors can also use known agonists and antagonists for other G-protein coupled receptors and the natural ligands disclosed herein as negative or positive controls to assess activity of tested compounds. In assays for identifying modulatory compounds (e.g., agonists, antagonists), changes in the level of ions in the cytoplasm or membrane voltage are monitored using an ion sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as Gα15 and Gα16 can be used in the assay of choice (Wilkie et al., Proc. Nat'l Acad. Sci. USA 88:10049 10053 (1991)). Such promiscuous G-proteins allow coupling of a wide range of receptors to signal transduction pathways in heterologous cells.

As noted above, receptor activation by ligand binding typically initiates subsequent intracellular events, e.g., increases in second messengers such as IP3, which releases intracellular stores of calcium ions. Activation of some G-protein coupled receptors stimulates the formation of inositol triphosphate (IP3) through phospholipase C-mediated hydrolysis of phosphatidylinositol (Berridge & Irvine, Nature 312:315 21 (1984)). IP3 in turn stimulates the release of intracellular calcium ion stores. Thus, a change in cytoplasmic calcium ion levels, or a change in second messenger levels such as IP3 can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated by ligand binding, result in a change in the level of intracellular cyclic nucleotides, e.g., cAMP or cGMP, by activating or inhibiting downstream effectors such as adenylate cyclase. In one embodiment, changes in intracellular cAMP or cGMP can be measured using immunoassays. The method described in Offermanns & Simon, J. Biol. Chem. 270:15175 15180 (1995) may be used to determine the level of cAMP. Also, the method described in Felley-Bosco et al., Am. J. Resp. Cell and Mol. Biol. 11:159 164 (1994) may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436,128, herein incorporated by reference. Briefly, the assay involves labeling of cells with 3H-myoinositol for 48 or more hrs. The labeled cells are treated with a compound for one hour. The treated cells are lysed and extracted in chloroform-methanol-water after which the inositol phosphates are separated by ion exchange chromatography and quantified by scintillation counting. Fold stimulation is determined by calculating the ratio of counts per minute (cpm) in the presence of agonist to cpm in the presence of buffer control. Likewise, fold inhibition is determined by calculating the ratio of cpm in the presence of antagonist to cpm in the presence of buffer control (which may or may not contain an agonist).

In another embodiment, transcription levels can be measured to assess the effects of a test compound on ligand-induced signal transduction. A host cell containing the protein of interest is contacted with a test compound in the presence of the natural ligand for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter genes may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, the protein of interest can be used as an indirect reporter via attachment to a second reporter such as green fluorescent protein (see, e.g., Mistili & Spector, Nature Biotechnology 15:961 964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

Samples that are treated with a GPCR antagonist are compared to control samples comprising the natural ligand without the test compound to examine the extent of modulation. Control samples (untreated with activators or inhibitors) are assigned a relative GPCR activity value of 100 Inhibition of a GPCR is achieved when the GPCR activity value relative to the control is about 90%, optionally 50%, or optionally 25%. Activation of a GPCR is achieved when the GPCR activity value relative to the control is 110%, optionally 150%, 200-500%, or 1000-2000%.

Determining β-Arrestin/GRK-Mediated Signal Transduction

The ability of the compounds of the present invention to activate β-arrestin/GRK-mediated signal transduction via the AT1 angiotensin receptor may be measured using any assay known in the art used to detect β-arrestin/GRK-mediated signal transduction via the AT1 angiotensin receptor, or the absence of such signal transduction. Generally, activated GPCRs become substrates for kinases that phosphorylate the C-terminal tail of the receptor (and possibly other sites as well). Thus, an antagonist will inhibit the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors.

The proximal event in β-arrestin function mediated by GPCRs is recruitment to receptors following ligand binding and receptor phosphorylation by GRK's. Thus, measure of β-arrestin recruitment was used to determine ligand efficacy for β-arrestin function.

Peptides, Derivatives and Mimetics

The terms "peptidyl" and "peptidic" as used throughout the specification and claims are intended to include active derivatives, variants, and/or mimetics of the peptides according to the present embodiments. Peptidic compounds are structurally similar bioactive equivalents of the peptides according to the present embodiments. By a "structurally similar bioactive equivalent" is meant a peptidyl compound with structure sufficiently similar to that of an identified bioactive peptide to produce substantially equivalent therapeutic effects. For example, peptidic compounds derived from the amino acid sequence of the peptide, or having an amino acid sequence backbone of the peptide, are considered structurally similar bioactive equivalents of the peptide.

The term "variant" refers to a protein or polypeptide in which one or more amino acid substitutions, deletions, and/or insertions are present as compared to the amino acid sequence of an protein or peptide and includes naturally occurring allelic variants or alternative splice variants of an protein or peptide. The term "variant" includes the replacement of one or more amino acids in a peptide sequence with a similar or homologous amino acid(s) or a dissimilar amino acid(s). Preferred variants include alanine substitutions at one or more of amino acid positions. Other preferred substitutions include conservative substitutions that have little or no effect on the overall net charge, polarity, or hydrophobicity of the protein. Conservative substitutions are set forth in the table below. According to some embodiments, the CK polypeptides have at least 60%, 65%, 70%, 75%, 80%, 85%, 88%, 95%, 96%, 97%, 98% or 99% sequence identity with the amino acid or amino acid analogue sequences of the preferred embodiments.

Conservative Amino Acid Substitutions

| | |
|---|---|
| Basic: | arginine |
| | lysine |
| | histidine |
| Acidic: | glutamic acid |
| | aspartic acid |
| Uncharged | glutamine |
| Polar: | asparagine |
| | serine |
| | threonine |
| | tyrosine |
| Non-Polar: | phenylalanine |
| | tryptophan |
| | cysteine |
| | glycine |
| | alanine |
| | valine |
| | praline |
| | methionine |
| | leucine |
| | isoleucine |

The table below sets out another scheme of amino acid substitution:

| Original Residue | Substitutions |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Other variants can consist of less conservative amino acid substitutions, such as selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to have a more significant effect on function are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine. Other variants include those designed to either generate a novel glycosylation and/or phosphorylation site(s), or those designed to delete an existing glycosylation and/or phosphorylation site(s). Variants include at least one amino acid substitution at a glycosylation site, a proteolytic cleavage site and/or a cysteine residue. Variants also include proteins and peptides with additional amino acid residues before or after the protein or peptide amino acid sequence on linker peptides. The term "variant" also encompasses polypeptides that have the amino acid sequence of the proteins/peptides of the present invention with at least one and up to 25 (e.g., 1, 2, 3, 4, 5, 6, 7, 8, 9, 10, 15, 20) additional amino acids flanking either the 3' or 5' end of the amino acid sequence or both.

The term "variant" also refers to a protein that is at least 60 to 99 percent identical (e.g., 60, 65, 70, 75, 80, 85, 90, 95, 98, 99, or 100%, inclusive) in its amino acid sequence of the proteins of the present invention as determined by standard methods that are commonly used to compare the similarity in position of the amino acids of two polypeptides. The degree of similarity or identity between two proteins can be readily calculated by known methods. Preferred methods to determine identity are designed to give the largest match between the sequences tested. Methods to determine identity and similarity are codified in publicly available computer programs. Variants will typically have one or more (e.g., 2, 3, 4, 5, etc.) amino acid substitutions, deletions, and/or insertions as compared with the comparison protein or peptide, as the case may be.

The compounds of the present invention include compounds having one of the general formulas described herein, in addition to derivatives and/or mimetics thereof.

The term "derivative" refers to a chemically modified protein or polypeptide that has been chemically modified either by natural processes, such as processing and other post-translational modifications, but also by chemical modification techniques, as for example, by addition of one or more polyethylene glycol molecules, sugars, phosphates, and/or other such molecules, where the molecule or molecules are not naturally attached to wild-type proteins. Derivatives include salts. Such chemical modifications are well described in basic texts and in more detailed monographs, as well as in a voluminous research literature, and they are well known to those of skill in the art. It will be appreciated that the same type of modification may be present in the same or varying degree at several sites in a given protein or polypeptide. Also, a given protein or polypeptide may contain many types of modifications. Modifications can occur anywhere in a protein or polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, Proteins—Structure And Molecular Properties, 2nd Ed., T. E. Creighton, W. H. Freeman and Company, New York (1993) and Wold, F., "Posttranslational Protein Modifications: Perspectives and Prospects," pgs. 1-12 in Posttranslational Covalent Modification Of Proteins, B. C. Johnson, Ed., Academic Press, New York (1983); Seifter et al., Meth. Enzymol. 182:626-646 (1990) and Rattan et al., "Protein Synthesis: Posttranslational Modifications and Aging," Ann. N.Y. Acad. Sci. 663: 48-62 (1992). The term "derivatives" include chemical modifications resulting in the protein or polypeptide becoming branched or cyclic, with or without branching. Cyclic, branched and branched circular proteins or polypeptides may result from post-translational natural processes and may be made by entirely synthetic methods, as well.

According to some embodiments, the compounds of the present invention may optionally include compounds wherein the N-terminus is derivatized to a —NRR$^1$ group; to a —NRC(O)R group; to a —NRC(O)OR group; to a —NRS(O)$_2$R group; to a —NHC(O)NHR group, where R and R$^1$ are hydrogen or lower alkyl with the proviso that R and R$^1$ are not both hydrogen; to a succinimide group; to a benzyloxycarbonyl-NH—(CBZ—CH—) group; or to a benzyloxycarbonyl-NE-group having from 1 to 3 substituents on the phenyl ring selected from the group consisting of lower alkyl, lower alkoxy, chloro, and bromo.

According to some embodiments, the compounds of the present invention may optionally include compounds wherein the C terminus is derivatized to —C(O)R$^2$ where R$^2$ is selected from the group consisting of lower alkoxy, and —NR$^3$R$^4$ where R$^3$ and R$^4$ are independently selected from the group consisting of hydrogen and lower alkyl.

The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to the embodiments provide a spatial arrangement of reactive chemical moieties that closely resemble the three-dimensional arrangement of active groups in the peptide on which the peptide mimetic is based. As a result of this similar active-site geometry, the peptide mimetic has effects on biological systems that are similar to the biological activity of the peptide.

The peptides and peptide mimetics included in the compositions of the invention are 6 to 25, 6 to 20, 6 to 15, 6 to 10, 6 to 9, 6 to 8, 7 to 25, 7 to 20, 7 to 15, 7 to 12, 7 to 10, 7 to 9, 7 to 8, 8 to 25, 8 to 20, 8 to 15, 8 to 12, 8 to 10, 8 to 9, 9 to 25, 9 to 20, 9 to 18, 9 to 15, 9 to 14, 9 to 12, 10 to 25, 10 to 20, 10 to 15, 10 to 14, 10 to 12, 12 to 25 or 12 to 20 amino acids or amino acid analogues in length.

The peptide mimetics of the embodiments are preferably substantially similar in both three-dimensional shape and biological activity to the peptides described herein. According to some embodiments, peptide mimetics of the present invention have protective groups at one or both ends of the compounds of the inventions, and/or replacement of one or more peptide bonds with non-peptide bonds. Such modifications may render the compounds less susceptible to proteolytic cleavage than the compound itself. For instance, one or more peptide bonds can be replaced with an alternative type of covalent bond (e.g., a carbon-carbon bond or an acyl bond). Peptide mimetics can also incorporate amino-terminal or carboxyl terminal blocking groups such as t-butyloxycarbonyl, acetyl, alkyl, succinyl, methoxysuccinyl, suberyl, adipyl, azelayl, dansyl, benzyloxycarbonyl, fluorenyl-methoxycarbonyl, methoxyazelayl, methoxyadipyl, methoxysuberyl, and 2,4,-dinitrophenyl, thereby rendering the mimetic less susceptible to proteolysis. Non-peptide bonds and carboxyl- or amino-terminal blocking groups can be used singly or in combination to render the mimetic less susceptible to proteolysis than the corresponding peptide/compound. Additionally, substitution of D-amino acids for the normal L-stereoisomer can be effected, e.g. to increase the half-life of the molecule.

Thus, according to some embodiments, the compounds of the present invention may optionally include a pseudopeptide bond wherein one or more of the peptidyl [—C(O)NR—] linkages (bonds) have been replaced by a non-peptidyl linkage such as —CH$_2$—NH—, —CH$_2$—CH$_2$—SO—, —CH$_2$—SO$_2$—, —NH—CO—, or —CH=CH— replacing a peptide bond (—CO—NH—). According to some embodiments, the compounds of the present invention may optionally include a pseudopeptide bond wherein one or more of the peptidyl [—C(O)NR—] linkages (bonds) have been replaced by a non-peptidyl linkage such as a —CH$_2$-carbamate linkage [—CH$_2$—OC(O)NR—]; a phosphonate linkage; a —CH$_2$-sulfonamide [—CH$_2$—S(O)$_2$NR—] linkage; a urea [—NHC(O)NH—] linkage; a —CH$_2$-secondary amine linkage; or an alkylated peptidyl linkage [—C(O)NR$^6$— where R$^6$ is lower alkyl]. Preferred mimetics have from zero to all of the —C(O)NH— linkages of the of the present invention replaced by a pseudopeptide.

Examples of methods of structurally modifying a peptide known in the art to create a peptide mimetic include the inversion of backbone chiral centers leading to D-amino acid residue structures that may, particularly at the N-terminus, lead to enhanced stability for proteolytical degradation without adversely affecting activity. An example is given in the paper "Tritriated D-ala$^1$-Peptide T Binding", Smith C. S. et al., Drug Development Res., 15, pp. 371-379 (1988). A second method is altering cyclic structure for stability, such as N to C interchain imides and lactames (Ede et al. in Smith and Rivier (Eds.) "Peptides: Chemistry and Biology", Escom, Leiden (1991), pp. 268-270). An example of this is given in conformationally restricted thymopentin-like compounds, such as those disclosed in U.S. Pat. No. 4,457,489 (1985), Goldstein, G. et al., the disclosure of which is incorporated by reference herein in its entirety. A third method is to substitute peptide bonds in the peptide by pseudopeptide bonds that confer resistance to proteolysis. The synthesis of peptides containing pseudopeptide bonds such as —CH$_2$—NH—, —CH$_2$—S—, —CH$_2$—SO—, —CH$_2$—SO$_2$—, —NH—CO— or —CH=CH— is performed either by solution methods or in a combined procedure with solid-phase synthesis using standard methods of organic chemistry. Thus, for example, the introduction of the —CH$_2$—NH— bond is accomplished by preparing in solution the aldehyde Fmoc-NH—CHR—CHO according to the technique described by FEHRENTZ and CASTRO (Synthesis, 676-678, 1983) and condensing it with the growing peptide chain, either on a solid phase according to the technique described by SASAKI and COY (Peptides, 8, 119-121, 1988), or in solution.

Pharmaceutical Compositions/Formulations

Pharmaceutical compositions for use in the present invention can be formulated by standard techniques using one or more physiologically acceptable carriers or excipients. In a preferred embodiment of the invention, the formulations may contain a buffer and/or a preservative. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally in a vehicle comprising one or more pharmaceutically acceptable carriers, the proportion of which is determined by the solubility and chemical nature of the peptide, chosen route of administration and standard biological practice.

According to some embodiments, pharmaceutical compositions are provided comprising effective amounts of one or more compound(s) of the present invention together with, for example, pharmaceutically acceptable diluents, preservatives, solubilizers, emulsifiers, adjuvants and/or other carriers. Such compositions include diluents of various buffer content (e.g., TRIS or other amines, carbonates, phosphates, amino acids, for example, glycinamide hydrochloride (especially in the physiological pH range), N-glycylglycine, sodium or potassium phosphate (dibasic, tribasic), etc. or TRIS-HCl or acetate), pH and ionic strength; additives such as detergents and solubilizing agents (e.g., surfactants such as Pluronics, Tween 20, Tween 80 (Polysorbate 80), Cremophor, polyols such as polyethylene glycol, propylene glycol, etc.), anti-oxidants (e.g., ascorbic acid, sodium metabisulfite), preservatives (e.g., Thimersol, benzyl alcohol, parabens, etc.) and bulking substances (e.g., sugars such as sucrose, lactose, mannitol, polymers such as polyvinylpyrrolidones or dextran, etc.); and/or incorporation of the material into particulate preparations of polymeric compounds such as polylactic acid, polyglycolic acid, etc. or into liposomes. Hyaluronic acid may also be used. Such compositions can be employed to influence the physical state, stability, rate of in vivo release, and rate of in vivo clearance of a compound of the present invention. See, e.g., *Remington's Pharmaceutical Sciences*, 18th Ed. (1990, Mack Publishing Co., Easton, Pa. 18042) pages 1435-1712 which are herein incorporated by reference. The compositions can, for example, be prepared in liquid form, or can be in dried powder, such as lyophilized form. Particular methods of administering such compositions are described infra.

Where a buffer is to be included in the formulations of the invention, the buffer is selected from the group consisting of sodium acetate, sodium carbonate, citrate, glycylglycine, histidine, glycine, lysine, arginin, sodium dihydrogen phosphate, disodium hydrogen phosphate, sodium phosphate, and tris(hydroxymethyl)-aminomethan, or mixtures thereof. Each one of these specific buffers constitutes an alternative embodiment of the invention. In a preferred embodiment of the invention the buffer is glycylglycine, sodium dihydrogen phosphate, disodium hydrogen phosphate, sodium phosphate or mixtures thereof.

Where a pharmaceutically acceptable preservative is to be included in the formulations of the invention, the preservative is selected from the group consisting of phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof. Each one of these specific preservatives constitutes an alternative embodiment of the invention. In a preferred embodiment of the invention the preservative is phenol or m-cresol.

In a further embodiment of the invention the preservative is present in a concentration from about 0.1 mg/ml to about 50 mg/ml, more preferably in a concentration from about 0.1 mg/ml to about 25 mg/ml, and most preferably in a concentration from about 0.1 mg/ml to about 10 mg/ml.

The use of a preservative in pharmaceutical compositions is well-known to the skilled person. For convenience reference is made to Remington: The Science and Practice of Pharmacy, 19th edition, 1995.

In a further embodiment of the invention the formulation may further comprise a chelating agent where the chelating agent may be selected from salts of ethlenediaminetetraacetic acid (EDTA), citric acid, and aspartic acid, and mixtures thereof. Each one of these specific chelating agents constitutes an alternative embodiment of the invention.

In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml.

The use of a chelating agent in pharmaceutical compositions is well-known to the skilled person. For convenience reference is made to Remington: The Science and Practice of Pharmacy, 19th edition, 1995.

In a further embodiment of the invention the formulation may further comprise a stabiliser selected from the group of high molecular weight polymers or low molecular compounds where such stabilizers include, but are not limited to, polyethylene glycol (e.g. PEG 3350), polyvinylalcohol (PVA), polyvinylpyrrolidone, carboxymethylcellulose, different salts (e.g. sodium chloride), L-glycine, L-histidine, imidazole, arginine, lysine, isoleucine, aspartic acid, tryptophan, threonine and mixtures thereof. Each one of these specific stabilizers constitutes an alternative embodiment of the invention. In a preferred embodiment of the invention the stabiliser is selected from the group consisting of L-histidine, imidazole and arginine.

In a further embodiment of the invention the high molecular weight polymer is present in a concentration from 0.1 mg/ml to 50 mg/ml. In a further embodiment of the invention the high molecular weight polymer is present in a concentration from 0.1 mg/ml to 5 mg/ml. In a further embodiment of the invention the high molecular weight polymer is present in a concentration from 5 mg/ml to 10 mg/ml. In a further embodiment of the invention the high molecular weight polymer is present in a concentration from 10 mg/ml to 20 mg/ml. In a further embodiment of the invention the high molecular weight polymer is present in a concentration from 20 mg/ml to 30 mg/ml. In a further embodiment of the invention the high molecular weight polymer is present in a concentration from 30 mg/ml to 50 mg/ml.

In a further embodiment of the invention the low molecular weight compound is present in a concentration from 0.1 mg/ml to 50 mg/ml. In a further embodiment of the invention the low molecular weight compound is present in a concentration from 0.1 mg/ml to 5 mg/ml. In a further embodiment of the invention the low molecular weight compound is present in a concentration from 5 mg/ml to 10 mg/ml. In a further embodiment of the invention the low molecular weight compound is present in a concentration from 10 mg/ml to 20 mg/ml. In a further embodiment of the invention the low molecular weight compound is present in a concentration from 20 mg/ml to 30 mg/ml. In a further embodiment of the invention the low molecular weight compound is present in a concentration from 30 mg/ml to 50 mg/ml.

The use of a stabilizer in pharmaceutical compositions is well-known to the skilled person. For convenience reference is made to Remington: The Science and Practice of Pharmacy, 19th edition, 1995.

In a further embodiment of the invention the formulation of the invention may further comprise a surfactant where a surfactant may be selected from a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g. Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, docusate calcium, docusate potassium, SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propane-sulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, zwitterionic surfactants (e.g. N-alkyl-N,N-dimethylammonio-1-propanesulfonates, 3-cholamido-1-propyldimethylammonio-1-propane-sulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives—(e.g. sodium tauro-dihydrofusidate etc.), long-chain fatty acids and salts thereof C6-C12 (e.g. oleic acid and caprylic acid), acylcarnitines and derivatives, $N_\alpha$-acylated derivatives of lysine, arginine or histidine, or side-chain acylated derivatives of lysine or arginine, $N_\alpha$-acylated derivatives of dipeptides comprising any combination of lysine, arginine or histidine and a neutral or acidic amino acid, $N_\alpha$-acylated derivative of a tripeptide comprising any combination of a neutral amino acid and two charged amino acids, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: The Science and Practice of Pharmacy, 19th edition, 1995.

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The formulations of the invention may be prepared by conventional techniques, e.g. as described in Remington's Pharmaceutical Sciences, 1985 or in Remington: The Science and Practice of Pharmacy, 19th edition, 1995, where such conventional techniques of the pharmaceutical industry involve dissolving and mixing the ingredients as appropriate to give the desired end product.

The phrase "pharmaceutically acceptable" or "therapeutically acceptable" refers to molecular entities and compositions that are physiologically tolerable and preferably do not typically produce an allergic or similar untoward reaction, such as gastric upset, dizziness and the like, when administered to a human. Preferably, as used herein, the term "pharmaceutically acceptable" means approved by a regulatory agency of the Federal or a State government or listed in the U.S. Pharmacopeia or other generally recognized pharmacopeia (e.g., Remington's Pharmaceutical Sciences, Mack Publishing Co. (A. R. Gennaro edit. 1985)) for use in animals, and more particularly in humans.

Administration of the compounds of the present invention may be carried out using any method known in the art. For example, administration may be transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, or oral administration. Preferably, a pharmaceutical composition of the present invention can be for administration for injection, or for oral, pulmonary, nasal, transdermal, ocular administration.

For oral administration, the peptide or a therapeutically acceptable salt thereof can be formulated in unit dosage forms such as capsules or tablets. The tablets or capsules may be prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For topical administration, the peptide can be formulated in a pharmaceutically acceptable vehicle containing 0.1 to 10 percent, preferably 0.5 to 5 percent, of the active compound(s). Such formulations can be in the form of a cream, lotion, sublingual tablet, aerosols and/or emulsions and can be included in a transdermal or buccal patch of the matrix or reservoir type as are conventional in the art for this purpose.

For parenteral administration, the compounds of the present invention are administered by either intravenous, subcutaneous, or intramuscular injection, in compositions with pharmaceutically acceptable vehicles or carriers. The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

For administration by injection, it is preferred to use the compound(s) in solution in a sterile aqueous vehicle which may also contain other solutes such as buffers or preservatives as well as sufficient quantities of pharmaceutically acceptable salts or of glucose to make the solution isotonic. In some embodiments, the pharmaceutical compositions of the present invention may be formulated with a pharmaceutically acceptable carrier to provide sterile solutions or suspensions for injectable administration. In particular, injectables can be prepared in conventional forms, either as liquid solutions or suspensions, solid forms suitable for solution or suspensions in liquid prior to injection or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized. Suitable pharmaceutical carriers are described in "Remington's pharmaceutical Sciences" by E. W. Martin.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch. For intranasal administration the compounds of the invention may be used, for example, as a liquid spray, as a powder or in the form of drops.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

Dosages

The compounds of the present invention may be administered to a patient at therapeutically effective doses to prevent, treat, or control diseases and disorders mediated, in whole or in part, by a GPCR-ligand interaction of the present invention. Pharmaceutical compositions comprising one or more of compounds of the present invention may be administered to a patient in an amount sufficient to elicit an effective protective or therapeutic response in the patient. An amount adequate to accomplish this is defined as "therapeutically effective dose." The dose will be determined by the efficacy of the particular compound employed and the condition of the subject, as well as the body weight or surface area of the area to be treated. The size of the dose also will be determined by the existence, nature, and extent of any adverse effects that accompany the administration of a particular compound or vector in a particular subject.

Toxicity and therapeutic efficacy of such compounds can be determined by standard pharmaceutical procedures in cell cultures or experimental animals, for example, by determining the LD50 (the dose lethal to 50% of the population) and the ED50 (the dose therapeutically effective in 50% of the population). The dose ratio between toxic and therapeutic effects is the therapeutic index and can be expressed as the ratio, LD50/ED50. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. The dosage of such compounds lies preferably within a range of circulating concentrations that include the ED50 with little or no toxicity. The dosage can vary within this range depending upon the dosage form employed and the route of administration. For any compound used in the methods of the invention, the therapeutically effective dose can be estimated initially from cell culture assays. A dose can be formulated in animal models to achieve a circulating plasma concentration range that includes the IC50 (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. An ordinarily skilled physician or veterinarian can readily determine and prescribe the effective amount of the drug required to prevent, counter or arrest the progress of the condition. In general it is contemplated that an effective amount would be from 0.001 mg/kg to 10 mg/kg body weight, and in particular from 0.01 mg/kg to 1 mg/kg body weight. More specifically it is contemplated that an effective amount would be to continuously infuse by intravenous administration from 0.01 micrograms/kg body weight/min to 100 micrograms/kg body weight/min for a period of 12 hours to 14 days. It may be appropriate to administer the required dose as two, three, four or more sub-doses at appropriate intervals throughout the day. Said sub-doses may be formulated as unit dosage forms, for example, containing 0.01 to 500 mg, and in particular 0.1 mg to 200 mg of active ingredient per unit dosage form.

Preferably, the pharmaceutical preparation is in a unit dosage form. In such form, the preparation is subdivided into suitably sized unit doses containing appropriate quantities of the active component, e.g., an effective amount to achieve the desired purpose. The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application. The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

Medical Use

The compositions of this invention are useful for treating any cardiovascular disorder that will respond favorably to a decrease in blood pressure. These disorders include chronic hypertension, hypertensive crisis (an acute hypertensive emergency), acute congestive heart failure, angina, acute myocardial infarction, left ventricular failure, cerebrovascular insufficiency, and intracranial haemorrhage. Intravenous injection is a preferred method for treating acute cardiovascular disorders. Such a method would comprise administering a therapeutically effective amount of one or more compounds of the present invention to a subject in need thereof. Examples of acute cardiovascular disorders include, but are not limited to, hypertensive crisis, toxemia of pregnancy, and acute congestive heart failure.

Combination Therapies

The invention also provides a method of treating any cardiovascular or cardiorenal disorder by administering one or more of the compositions of the invention as described above in combination with other drugs for the treatment of cardiovascular and/or cardiorenal disorders. These other drugs include diuretics such as furosemide; vasodilators such as nitroglycerin, nitroprusside, brain natriuretic peptide (BNP), or analogues thereof; inotropes such as dobutamine; angiotensin convertin enzyme (ACE) inhibitors such as captopril and enalapril; β blockers such as carvedilol and propranolol; angiotensin receptor blockers (ARBs) such as valsartan and candesartan; and/or aldosterone antagonists such as spironolactone.

In the combination therapies of the invention, one or more compositions of the invention are coadministered with one or more drugs for the treatment of cardiovascular and/or cardiorenal disorders to increase efficacy of treatment of cardiovascular and/or cardiorenal disorders and to reduce side effects associated with high doses of these therapeutics.

The combination therapies of the invention described above have synergistic and additive therapeutic effects. Synergy is defined as the interaction of two or more agents so that their combined effect is greater than the sum of their individual effects. For example, if the effect of drug A alone in treating a disease is 25%, and the effect of drug B alone in treating a disease is 25%, but when the two drugs are combined the effect in treating the disease is 75%, the effect of A and B is synergistic.

Additivity is defined as the interaction of two or more agents so that their combined effect is the same as the sum of their individual effects. For example, if the effect of drug A alone in treating a disease is 25%, and the effect of drug B alone in treating a disease is 25%, but when the two drugs are combined the effect in treating the disease is 50%, the effect of A and B is additive.

An improvement in the drug therapeutic regimen can be described as the interaction of two or more agents so that their combined effect reduces the incidence of adverse event (AE) of either or both agents used in co-therapy. This reduction in the incidence of adverse effects can be a result of, e.g., administration of lower dosages of either or both agent used in the co-therapy. For example, if the effect of Drug A alone is 25% and has an adverse event incidence of 45% at labeled dose; and the effect of Drug B alone is 25% and has an adverse event incidence of 30% at labeled dose, but when the two drugs are combined at lower than labeled doses of each, if the overall effect is 35% (an improvement, but not synergistic or additive) and the adverse incidence rate is 20%, there is an improvement in the drug therapeutic regimen.

DEFINITIONS

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the invention will be apparent from the following detailed description and claims.

For the purposes of promoting an understanding of the embodiments described herein, reference will be made to preferred embodiments and specific language will be used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth. Thus, for example, a reference to "a host cell" includes a plurality of such host cells, and a reference to "an antibody" is a reference to one or more antibodies and equivalents thereof known to those skilled in the art, and so forth.

EXAMPLES

The following examples are illustrative, but not limiting, of the methods and compositions of the present invention. Other suitable modifications and adaptations of the variety of conditions and parameters normally encountered in therapy and that are obvious to those skilled in the art are within the spirit and scope of the embodiments.

Example 1

Synthesis of Compounds

Peptides and intermediates described herein were prepared by the solid-phase method of peptide synthesis. (cf. R. Merrifield J. Am. Chem. Soc. 1964, 85, 2149; M. Bodansky, "Principles of Peptide Synthesis." Springer-Verlag, 1984.) The peptide synthesis and purification procedures employed were standard methods well described in the art, including, but not limited to, amino acid coupling procedures, wash steps, deprotection procedures, resin cleavage procedures, and ion exchange and HPLC purification methods using commercial automated peptide synthesizers and commercially available resins and protected amino acids. More specifically, the peptides were synthesized from their C-terminus by stepwise addition of Fmoc-protected amino acids (pre-activated or in situ activated) and deprotection of the Fmoc group with piperidine to an acid labile linker attached to an insoluble support resin. Following synthesis, the resin bound peptide was side chain-deprotected and detached from the resin with trifluoroacetic acid and cation scavengers. Peptides were purified by aqueous extraction or by precipitation from organic solvents such as ether or t-butyl methyl ether followed by centrifugation and decanting and/or by HPLC and lyophilization.

Example 2

B-Arrestin Recruitment Assay

The proximal event in β-arrestin function mediated by GPCRs is recruitment to receptors following ligand binding and receptor phosphorylation by GRK's. Thus, the measure of β-arrestin recruitment was used to determine ligand efficacy for β-arrestin function.

B-arrestin-2 recruitment to the human and rat angiotensin 2 type 1 receptor (human AT1R and rat AT1aR, respectively) was measured with the PathHunter™ β-arrestin assay (DiscoveRx Corporation, Fremont Calif.). Cells, plasmid(s), and detection reagent(s) were purchased from DiscoveRx, and assays were performed per manufacturer's instructions. Human AT1R and rat AT1aR were cloned into the pCMV-ProLink vector, verified by sequencing, and transfected into PathHunter β-arrestin HEK293 cells. Stably transfected clonal cell lines were selected with Hygromycin and G418. These clonal cell lines were used for all experiments.

For assays, 25,000 cells were seeded per well in 96-well microplates in volumes of 90 μL and allowed to grow overnight at 37° C. in 5% $CO_2$. Peptides of the invention were dissolved in deionized water to a concentration of 1 mM. Peptides were then further diluted in assay buffer (Hank's balanced salt solution with 20 mM HEPES) to add peptide to the cells to reach final concentrations ranging from 10 μM to 1 pM. Cells were then incubated for 60 minutes at 37° C. in 5% $CO_2$, followed by addition of 50 μL of PathHunter Detection Reagent to each well. The microplates were then incubated at room temperature for 60 minutes, and then luminescence was measured using a NOVOstar microplate reader purchased from BMG Labtech. B-arrestin-2 recruitment to receptors was measured as relative luminescence intensity expressed in arbitrary units. Results are displayed in Table 2 below.

Example 3

IP1 Accumulation Assay

A secondary measure of G protein coupling efficacy was also performed. IP3 is generated by activation of phospholipase C by Gα-q. IP3 is degraded to IP1, which can be forced to accumulate in cells by blocking degradation with lithium chloride. Thus we measured accumulation of IP1 to determine ligand efficacy for G protein activation.

IP1 accumulation generated by human and rat angiotensin 2 type 1 receptor (human AT1R and rat AT1aR, respectively) was measured with IP-One Tb kits purchased from Cisbio and used per the manufacturer's instructions. Clonal stably transfected cell lines expressing human AT1TR or rat AT1aR were used for all experiments.

For assays, 4,000 cells were seeded per well in 384-well small-volume microplates in volumes of 20 uL and allowed to grow overnight at 37° C. in 5% $CO_2$. Cell growth media was then replaced with stimulation buffer supplied by Cisbio containing 50 mM lithium chloride. Peptides TRV-120,001 through TRV-120,035 were dissolved in deionized water to a concentration of 1 mM. For agonist detection, peptides were then further diluted in stimulation buffer to add peptide to the cells to reach final concentrations ranging from 10 uM to 1 pM. For antagonist detection, peptides were then further diluted in stimulation buffer to add peptide to the cells to reach final concentrations ranging from 10 uM to 1 pM, and followed by addition of 10 nM AngII. Following addition of peptides, cells were incubated at 37° C. in 5% $CO_2$ for 30 minutes and then lysed with detection reagents added per manufacturer's instructions. Microplates were incubated for 60-90 minutes and then time-resolved fluorescence intensities were measured using a PHERAstar Plus microplate reader from BMG Labtech. IP1 accumulation was measured as change in ratio of time-resolved fluorescent intensities measured at 665 nm and 620 nm. Results are displayed in Table 2 below.

TABLE 2

| | Biological activity. | | | | | | | |
|---|---|---|---|---|---|---|---|---|
| | human AT1R | | | | rat AT1aR | | | |
| | b-arrestin2 | | IP One | | b-arrestin2 | | IP One | |
| # | EC50 (M) | Max (%) | EC50 (M) | Max (%) | EC50 (M) | Max (%) | EC50 (M) | Max (%) |
| AngII | 9.7E−09 | 99.0 | 2.6E−09 | 96.9 | 6.8E−09 | 97.0 | 1.3E−09 | 98.1 |
| Valsartan | inactive | | inactive | | inactive | | | |
| 2 | 4.5E−06 | 24.9 | inactive | | inactive | | 3.6E−07 | 33.8 |
| 3 | 4.5E−07 | 36.5 | inactive | | 1.2E−07 | 67.1 | 4.1E−08 | 19.6 |
| 5 | 1.6E−06 | 39.4 | 6.5E−08 | 18.1 | 1.9E−06 | 61.7 | 9.6E−08 | 24.8 |
| 6 | 9.2E−07 | 12.1 | 1.1E−07 | 14.1 | inactive | | 5.9E−08 | 21.9 |
| 7 | 1.1E−08 | 63.0 | inactive | | 7.5E−09 | 86.5 | 6.0E−09 | 9.3 |
| 8 | 2.1E−07 | 36.9 | inactive | | 2.0E−07 | 41.8 | 3.5E−08 | 11.3 |
| 9 | 9.2E−09 | 69.2 | inactive | | 4.8E−09 | 74.0 | 6.6E−09 | 9.5 |
| 10 | 1.6E−07 | 55.2 | inactive | | 1.8E−07 | 60.3 | 2.2E−07 | 13.3 |
| 11 | 3.4E−09 | 58.9 | inactive | | 6.1E−09 | 80.7 | 3.5E−09 | 24.4 |
| 12 | 3.9E−07 | 19.9 | 1.9E−07 | 20.7 | 1.2E−07 | 34.4 | 7.9E−08 | 44.9 |
| 13 | 4.6E−06 | 43.4 | inactive | | 4.3E−05 | 165.3 | Inactive | |
| 14 | 8.0E−09 | 59.3 | 1.6E−07 | 13.5 | 1.4E−08 | 79.0 | 3.2E−08 | 19.3 |
| 15 | 8.2E−07 | 44.3 | 2.5E−07 | 19.3 | 2.3E−07 | 62.1 | 7.7E−08 | 51.1 |
| 16 | 8.8E−07 | 56.9 | inactive | | 1.4E−07 | 76.9 | 9.2E−08 | 24.4 |
| 19 | 3.1E−08 | 67.9 | inactive | | 1.8E−08 | 91.2 | Inactive | |
| 20 | inactive | | inactive | | 3.6E−06 | 86.6 | Inactive | |
| 21 | 3.3E−08 | 64.4 | inactive | | 1.3E−08 | 82.7 | Inactive | |
| 22 | 2.7E−07 | 54.5 | inactive | | 2.7E−08 | 74.3 | 2.5E−07 | 5.2 |
| 23 | 4.4E−08 | 61.2 | inactive | | 3.9E−08 | 84.9 | 1.1E−08 | 10.3 |
| 24 | 4.8E−07 | 61.3 | inactive | | 6.3E−08 | 74.1 | 7.4E−08 | 15.1 |
| 25 | 2.1E−08 | 57.9 | inactive | | 1.5E−08 | 77.0 | 7.3E−09 | 14.1 |
| 26 | 7.5E−08 | 51.9 | inactive | | 3.8E−08 | 77.3 | Inactive | |
| 27 | 1.7E−08 | 58.1 | inactive | | 1.6E−08 | 84.2 | Inactive | |
| 28 | 2.0E−08 | 82.9 | inactive | | 1.9E−08 | 91.4 | 6.4E−08 | 24.6 |
| 29 | 5.9E−07 | 43.3 | inactive | | 2.0E−07 | 64.8 | Inactive | |
| 30 | 9.2E−09 | 68.2 | inactive | | 8.2E−09 | 80.4 | Inactive | |
| 31 | 1.0E−07 | 58.1 | inactive | | 3.7E−08 | 75.9 | 1.3E−08 | 6.2 |
| 32 | 7.9E−08 | 55.6 | inactive | | 4.3E−08 | 80.2 | 2.4E−08 | 6.8 |
| 33 | 4.0E−08 | 54.9 | inactive | | 3.1E−08 | 86.9 | Inactive | |
| 34 | 2.5E−08 | 53.0 | inactive | | 3.2E−08 | 81.7 | Inactive | |
| 35 | 1.2E−08 | 67.9 | 2.7E−09 | 7.1 | 9.3E−09 | 79.8 | 1.2E−08 | 30.5 |
| 36 | 1.2E−06 | 39.5 | inactive | | 1.9E−06 | 32.8 | 1.0E−07 | 19.2 |
| 37 | 1.7E−06 | 62.3 | inactive | | 1.9E−06 | 60.7 | 2.4E−07 | 14.7 |
| 38 | 6.8E−07 | 43.1 | inactive | | 2.5E−06 | 66.4 | 9.2E−07 | 20.8 |
| 44 | 8.0E−08 | 47.3 | inactive | | 6.5E−08 | 71.9 | 8.2E−09 | 14.6 |
| 57 | 4.3E−07 | 42.06 | 3.6E−09 | 10.03 | 4.5E−07 | 64.38 | 3.3E−07 | 35.26 |
| 58 | 3.3E−07 | 48.67 | inactive | | 2.6E−07 | 81.1 | 1.4E−06 | 9.937 |
| 59 | 1.4E−06 | 19.49 | inactive | | 8.2E−07 | 27.84 | Inactive | |
| 60 | 3.4E−07 | 44.02 | inactive | | 1.8E−07 | 79.27 | Inactive | |
| 61 | 1.2E−06 | 37.55 | inactive | | 2.1E−06 | 60.39 | Inactive | |
| 62 | 1.3E−06 | 24.68 | inactive | | 3.9E−06 | 44.19 | Inactive | |
| 63 | 5.3E−07 | 35.93 | inactive | | 5.3E−07 | 50.13 | Inactive | |
| 64 | 1.2E−06 | 20.39 | inactive | | 8.7E−07 | 26.95 | Inactive | |
| 65 | 2.0E−06 | 37.8 | inactive | | 2.8E−06 | 67.27 | Inactive | |
| 66 | 6.7E−06 | 30.56 | inactive | | 1.0E−05 | 58.54 | Inactive | |
| 67 | 1.0E−07 | 100.6 | inactive | | 6.3E−08 | 117 | Inactive | |
| 68 | 6.3E−07 | 39.2 | inactive | | 4.0E−07 | 59.2 | 2.5E−05 | 21.2 |
| 69 | 1.3E−08 | 53.9 | inactive | | 1.0E−08 | 88.3 | Inactive | |
| 70 | 1.6E−07 | 29.1 | inactive | | 7.9E−08 | 55.6 | Inactive | |
| 71 | 4.0E−07 | 52.7 | inactive | | 1.6E−07 | 81.7 | Inactive | |
| 72 | 6.3E−08 | 62.6 | inactive | | 2.5E−08 | 88.6 | Inactive | |
| 73 | 5.0E−06 | 46.8 | inactive | | 4.0E−06 | 77.4 | 2.5E−06 | 20.8 |
| 74 | 2.5E−07 | 47.8 | inactive | | 1.0E−07 | 59.0 | Inactive | |
| 75 | 2.5E−08 | 55.0 | inactive | | 1.3E−08 | 79.3 | 2.5E−05 | 26.7 |
| 76 | 1.6E−06 | 43.0 | inactive | | 6.3E−07 | 55.5 | Inactive | |
| 77 | 5.0E−08 | 97.5 | inactive | | 4.0E−08 | 110.5 | Inactive | |
| 78 | 1.0E−08 | 71.5 | inactive | | 5.0E−09 | 91.3 | Inactive | |
| 79 | 7.9E−09 | 64.8 | inactive | | 7.9E−09 | 93.6 | Inactive | |
| 80 | 1.0E−06 | 58.5 | inactive | | 5.0E−07 | 82.9 | Inactive | |
| 81 | 1.0E−05 | 32.6 | inactive | | 1.0E−05 | 54.3 | Inactive | |
| 82 | 3.2E−07 | 38.3 | inactive | | 1.3E−07 | 60.6 | Inactive | |
| 83 | 2.0E−07 | 34.3 | inactive | | 5.0E−08 | 70.2 | Inactive | |
| 84 | 3.2E−08 | 50.5 | inactive | | 1.6E−08 | 80.6 | Inactive | |
| 85 | 1.6E−06 | 51.1 | | | 5.0E−07 | 75.5 | 1.6E−05 | 23.4 |

Note:
inactive means that EC50 was greater than 10 uM.

Example 4

Calcium Mobilization Assay

G protein efficacy can be measured in many ways. GPCRs that couple to the $G_q$ subclass of heterotrimeric g proteins activate a wide array of signal transduction when activated by agonists. One of the most commonly measured pathways is activation of phospholipase C by Galpha-q, which cleaves phosphatidylinositol bisphosphate to release $IP_3$; $IP_3$ in turn releases calcium to the cytosol from intracellular stores via the $IP_3$ receptor. Thus we measured intracellular free calcium to determine ligand efficacy for G protein activation.

Intracellular free calcium generated by human and rat angiotensin 2 type 1 receptor (human AT1R and rat AT1aR, respectively) was measured with Fluo-4 NW kits purchased from Invitrogen and used per the manufacturer's instructions. Clonal stably transfected cell lines expressing human AT1TR or rat AT1aR were used for all experiments.

For assays, 25,000 cells were seeded per well in 96-well microplates in volumes of 90 uL and allowed to grow overnight at 37° C. in 5% $CO_2$. Fluo-4 NW dye was mixed with probenecid and assay buffer (Hank's balanced salt solution with 20 mM HEPES), and cell growth media was replace with this mixture, followed by incubation for 30-45 minutes at 37° C. in 5% $CO_2$. Peptides TRV-120,001 through TRV-120,035 were dissolved in deionized water to a concentration of 1 mM. Peptides were then further diluted in assay buffer (Hank's balanced salt solution with 20 mM HEPES) to add peptide to the cells to reach final concentrations ranging from 10 uM to 1 pM. Peptide was added to cells while fluorescence intensity was measured using a NOVOstar microplate reader purchased from BMG Labtech. Calcium mobilization was measured as relative fluorescence intensity expressed as fold over basal at 5 seconds and 20 seconds after ligand addition.

Example 5

Evaluation of SEQ ID NO:27 in Normal Rats

The effects of SEQ ID NO:27 on vascular and cardiac function were tested by i.v. infusion at doses ranging from 0.1-10 μg/kg/min in preliminary dosing experiments in normal anesthetized rats. Various hemodynamic measurements were made including mean arterial pressure, heart rate and pressure volume relationships. SEQ ID NO:27 produced a dose-dependent decrease in mean arterial pressure with little to no effect on HR. In addition, SEQ ID NO:27 increased the slope of the end systolic pressure volume relationship and preserved pre-recruitable stroke work, resulting in preservation of stroke volume in the background of a drop in vasoconstriction.

Example 6

Evaluation of SEQ ID NO:27 in a Paced Dog Model of Acute Heart Failure

SEQ ID NO:27 (0.01, 0.1, 1, 10 and 100 mcg/kg/min dose escalation, 30 minutes each dose) was also dosed in the paced heart failure model. In the paced dog model, pacemakers are implanted and the dog hearts are paced for ten days at a rate of 240 beats per minute, resulting in reduced left ventricular systolic function, right-side congestion, and an elevation in the renin-angiotensin system activity. In the heart failure dogs SEQ ID NO:27 produced a dose-dependent decrease in mean arterial pressure, systemic vascular resistance, pulmonary capillary wedge pressure, and right arterial pressure, and cardiac output was preserved in these animals. At the level of the kidney, there was a dose-dependent increase in renal blood flow resulting in a significant drop in renal vascular resistance. Urine sodium excretion modestly increased with urine output, urine potassium, and glomerular filtration rate being maintained.

While the invention has been described with reference to particularly preferred embodiments and examples, those skilled in the art recognize that various modifications may be made to the invention without departing from the spirit and scope thereof.

All of the above U.S. patents, U.S. patent application publications, U.S. patent applications, foreign patents, foreign patent applications and non-patent publications referred to in this specification and/or listed in the Application Data Sheet are incorporated herein by reference, in their entirety.

What is claimed is:

1. A method of treating a cardiovascular disorder in a subject, the method comprising administering to the subject a pharmaceutical composition comprising a peptide, or a pharmaceutically acceptable salt thereof, comprising the sequence of:

Sar-Arg-Val-Ww-Zz-His-Pro-Cc, wherein
Ww is L-tyrosine, 3-hydroxy-L-tyrosine, 3-fluoro-L-tyrosine, 2,6-difluoro-L-tyrosine, 3-nitro-L-tyrosine, 3,5-dinitro-L-tyrosine, 3-chloro-L-tyrosine, 2,6-dimethyl-L-tyrosine, 4-fluorophenyl-L-alanine, 3,5-dibromo-L-tyrosine, or O-allyl-L-tyrosine;
Zz is L-valine or L-isoleucine; and
Cc is D-alanine.

2. The method of claim 1, wherein the pharmaceutical composition comprises the peptide, or a pharmaceutically acceptable salt thereof.

3. The method of claim 2, wherein Zz is L-isoleucine.

4. The method of claim 2, wherein Ww is L-tyrosine, 3-hydroxy-L-tyrosine, 3-fluoro-L-tyrosine, 2,6-difluoro-L-tyrosine, 3-nitro-L-tyrosine, 3,5-dinitro-L-tyrosine, or 3-chloro-L-tyrosine.

5. The method of claim 4, wherein Zz is L-isoleucine.

6. The method of claim 2, wherein the peptide comprises the sequence of SEQ ID NO: 69, or a pharmaceutically acceptable salt thereof.

7. The method of claim 2, wherein the peptide comprises the sequence of SEQ ID NO: 67, or a pharmaceutically acceptable salt thereof.

8. The method of claim 2, wherein the peptide comprises the sequence of SEQ ID NO:27, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, or SEQ ID NO:76, or a pharmaceutically acceptable salt thereof.

9. The method of claim 2, wherein the peptide comprises the sequence of SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, or SEQ ID NO:76, or a pharmaceutically acceptable salt thereof.

10. The method of claim 2, wherein the pharmaceutical composition comprises a pharmaceutically acceptable carrier.

11. The method of claim 2, wherein the pharmaceutical composition comprises sterile water, phosphate buffered saline, or an aqueous glucose solution.

12. The method of claim 1, wherein the cardiovascular disorder is acute heart failure.

13. The method of claim 2, wherein the cardiovascular disorder is heart failure.

14. The method of claim 2, wherein the subject is a subject in need thereof.

15. The method of claim 1, wherein the cardiovascular disorder is selected from the group consisting of acute decompensated heart failure, chronic hypertension, hypertensive crisis, acute congestive heart failure, angina, acute myocardial infarction, left ventricular failure, cerebrovascular insufficiency, intracranial hemorrhage, essential hypertension, post-operative hypertension, hypertensive heart disease, hypertensive renal disease, renovascular hypertension, malignant hypertension, post-renal transplant patient stabilization, dilated cardiomyopathy, myocarditis, post-cardiac transplant patient stabilization, disorders associated with post-stent management, neurogenic hypertension, preeclampsia, and abdominal aortic aneurysm.

16. The method of claim 2, wherein the cardiovascular disorder is selected from the group consisting of acute decompensated heart failure, chronic hypertension, hypertensive crisis, acute congestive heart failure, angina, acute myocardial infarction, left ventricular failure, cerebrovascular insufficiency, intracranial hemorrhage, essential hypertension, post-operative hypertension, hypertensive heart disease, hypertensive renal disease, renovascular hypertension, malignant hypertension, post-renal transplant patient stabilization, dilated cardiomyopathy, myocarditis, post-cardiac transplant patient stabilization, disorders associated with post-stent management, neurogenic hypertension, preeclampsia, and abdominal aortic aneurysm.

17. The method of claim 14, wherein the heart failure is acute heart failure.

18. The method of claim 2, wherein the pharmaceutical composition is administered intravenously.

19. The method of claim 2, wherein the administration of the pharmaceutical composition maintains glomerular filtration rate in the subject.

20. The method of claim 2, wherein the administration of the pharmaceutical composition decreases vascular resistance in the subject.

21. A method of decreasing renal vascular resistance and/or maintaining glomerular filtration rate in a subject in need thereof, the method comprising administering to the subject in need thereof a pharmaceutical composition comprising a peptide, or a pharmaceutically acceptable salt thereof, comprising the sequence of:

Sar-Arg-Val-Ww-Zz-His-Pro-Cc,
wherein Ww is L-tyrosine, 3-hydroxy-L-tyrosine, 3-fluoro-L-tyrosine, 2,6-difluoro-L-tyrosine, 3-nitro-L-tyrosine, 3,5-dinitro-L-tyrosine, 3-chloro-L-tyrosine, 2,6-dimethyl-L-tyrosine, 4-fluorophenyl-L-alanine, 3,5-dibromo-L-tyrosine, or O-allyl-L-tyrosine;
Zz is L-valine or L-isoleucine; and
Cc is D-alanine.

22. The method of claim 21, wherein the pharmaceutical composition comprises a pharmaceutically acceptable carrier.

23. The method of claim 21, wherein the pharmaceutical composition comprises sterile water, phosphate buffered saline or an aqueous glucose solution.

24. The method of claim 21, wherein the peptide, or a pharmaceutically acceptable salt thereof, comprises the sequence of SEQ ID NO:27, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, or SEQ ID NO:76.

25. The method of claim 21, wherein the peptide, or a pharmaceutically acceptable salt thereof, comprises the sequence of SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, or SEQ ID NO:76.

* * * * *